US008790281B2

(12) United States Patent
Diederich et al.

(10) Patent No.: US 8,790,281 B2
(45) Date of Patent: Jul. 29, 2014

(54) METHOD OF THERMAL TREATMENT OF MYOLYSIS AND DESTRUCTION OF BENIGN UTERINE TUMORS

(75) Inventors: Chris J. Diederich, Novato, CA (US); Will Nau, Longmont, CO (US); Alison Jacoby, San Francisco, CA (US); Dana Deardorff, Lafayette, CO (US); Everette C. Burdette, Champaign, IL (US)

(73) Assignees: The Regents of the University of California, Oakland, CA (US); Acoustic Medsystems, Inc., Champaign, IL (US)

( * ) Notice: Subject to any disclaimer, the term of this patent is extended or adjusted under 35 U.S.C. 154(b) by 677 days.

(21) Appl. No.: 11/738,391

(22) Filed: Apr. 20, 2007

(65) Prior Publication Data

US 2007/0255267 A1    Nov. 1, 2007

Related U.S. Application Data

(60) Provisional application No. 60/793,750, filed on Apr. 20, 2006, provisional application No. 60/797,421, filed on May 3, 2006, provisional application No. 60/885,845, filed on Jan. 19, 2007.

(51) Int. Cl.

| | |
|---|---|
| A61H 1/00 | (2006.01) |
| A61N 7/02 | (2006.01) |
| A61N 7/00 | (2006.01) |
| A61N 5/10 | (2006.01) |
| A61N 5/04 | (2006.01) |
| A61B 17/22 | (2006.01) |

(52) U.S. Cl.
CPC ........... *A61N 7/02* (2013.01); *A61N 2007/0078* (2013.01); *A61N 2005/1094* (2013.01); *A61N 5/045* (2013.01); *A61B 17/2202* (2013.01)

USPC .................. 601/3; 601/2; 600/459; 600/466; 600/471; 606/27

(58) Field of Classification Search
USPC ............................................. 601/3
See application file for complete search history.

(56) References Cited

U.S. PATENT DOCUMENTS 5,273,045 A * 12/1993 Chihara et al. ................ 600/463
5,391,197 A *  2/1995 Burdette et al. ................... 601/3

(Continued)

FOREIGN PATENT DOCUMENTS

| EP | 0643 982 A1 | 3/1995 |
| EP | 1 579 889 A1 | 9/2005 |
| WO | 01/82778 A2 | 8/2001 |

OTHER PUBLICATIONS

Lee et al, "Arrays of Multielement Ultrasound Applicators for Interstitial Hyperthermia", IEEE Transactions on Biomedical Engineering, vol. 46, No. 7, Jul. 1999.*

(Continued)

*Primary Examiner* — Nicholas Evoy
(74) *Attorney, Agent, or Firm* — John P. O'Banion

(57) ABSTRACT

A high-power ultrasound heating applicator for minimally-invasive thermal treatment of uterine fibroids or myomas. High-intensity interstitial ultrasound, applied with minimally-invasive laparoscopic or hysteroscopic procedures, is used to effectively treat fibroids within the myometrium in lieu of major surgery. The applicators are configured with high-power capabilities and thermal penetration to treat large volumes of fibroid tissue (>70 cm$^3$) in short treatment times (3-20 minutes), while maintaining three-dimensional control of energy delivery to thermally destroy the target volume.

48 Claims, 18 Drawing Sheets

(56) References Cited

U.S. PATENT DOCUMENTS

| | | | | |
|---|---|---|---|---|
| 5,522,869 | A | * | 6/1996 | Burdette et al. .................. 601/3 |
| 5,549,638 | A | * | 8/1996 | Burdette ........................... 601/3 |
| 5,620,479 | A | * | 4/1997 | Diederich ........................ 601/3 |
| 5,630,837 | A | * | 5/1997 | Crowley ........................... 601/2 |
| 5,733,315 | A | * | 3/1998 | Burdette et al. ............... 601/97 |
| 6,059,731 | A | * | 5/2000 | Seward et al. ............... 600/459 |
| 6,066,096 | A | * | 5/2000 | Smith et al. .................... 600/439 |
| 6,117,101 | A | * | 9/2000 | Diederich et al. .............. 604/22 |
| 6,524,271 | B2 | * | 2/2003 | Brisken et al. .................. 604/22 |
| 6,537,306 | B1 | * | 3/2003 | Burdette et al. ............... 607/96 |
| 6,626,855 | B1 | * | 9/2003 | Weng et al. ...................... 601/3 |
| 6,645,202 | B1 | * | 11/2003 | Pless et al. ..................... 606/41 |
| 6,746,465 | B2 | * | 6/2004 | Diederich et al. ............ 606/192 |
| 6,971,394 | B2 | * | 12/2005 | Sliwa et al. ................... 128/898 |
| 7,628,785 | B2 | * | 12/2009 | Hadjicostis et al. ............ 606/27 |
| 7,854,733 | B2 | * | 12/2010 | Govari ............................. 606/27 |
| 2003/0069569 | A1 | * | 4/2003 | Burdette et al. ................ 606/27 |
| 2003/0114878 | A1 | * | 6/2003 | Diederich et al. ............ 606/192 |
| 2004/0044375 | A1 | * | 3/2004 | Diederich et al. .............. 607/27 |
| 2004/0147811 | A1 | * | 7/2004 | Diederich et al. ............ 600/207 |
| 2004/0242999 | A1 | | 12/2004 | Vitek et al. |
| 2004/0254570 | A1 | * | 12/2004 | Hadjicostis et al. ............ 606/27 |
| 2005/0085726 | A1 | * | 4/2005 | Lacoste et al. ................ 600/439 |
| 2005/0215990 | A1 | * | 9/2005 | Govari ............................ 606/27 |
| 2005/0255039 | A1 | * | 11/2005 | Desai ........................... 424/1.11 |
| 2005/0256405 | A1 | | 11/2005 | Makin et al. |
| 2014/0058294 | A1 | * | 2/2014 | Gross et al. ....................... 601/2 |

OTHER PUBLICATIONS

European Patent Office, Extended European Search Report issued on May 3, 2011 for related EPO Application No. 07761063.2 (pp. 1-7), with claims searched (pp. 7-12), counterpart to PCT/US2007/067145, claiming priority to USSN 601885,845, pp. 1-12.

ISA/US, international search report and written opinion issued on Jun. 13, 2008, related PCT Application No. PCT/US2007/067145, International Publication No. WO 2007/124458 dated Nov. 1, 2007, including specification and claims searched, pp. 1-63.

* cited by examiner

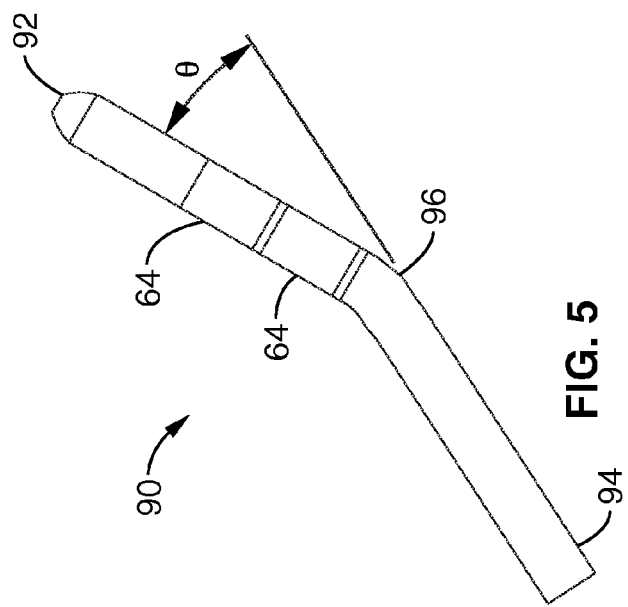
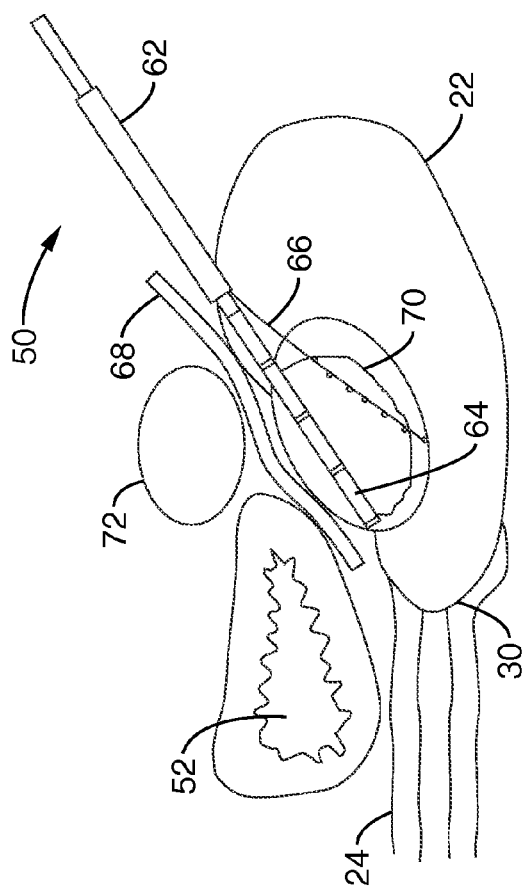
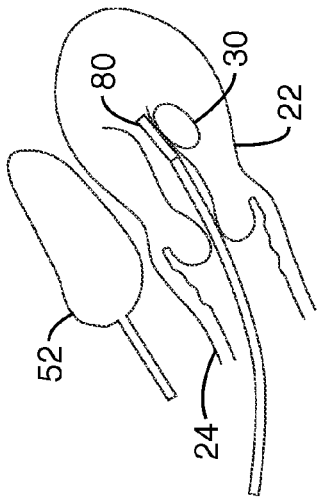

METHOD OF THERMAL TREATMENT OF MYOLYSIS AND DESTRUCTION OF BENIGN UTERINE TUMORS

CROSS-REFERENCE TO RELATED APPLICATIONS

This application claims priority from U.S. provisional application Ser. No. 60/885,845, filed on Jan. 19, 2007, incorporated herein by reference in its entirety, U.S. provisional application Ser. No. 60/797,421, filed on May 3, 2006, incorporated herein by reference in its entirety, and U.S. provisional application Ser. No. 60/793,750, filed on Apr. 20, 2006, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to treatment of uterine fibroids, and more particularly to ultrasound therapy of uterine fibroids.

2. Description of Related Art

Uterine fibroids, also known as leiomyomas or myomas, are the most common solid pelvic tumor occurring in women, and are the reason for nearly 30% of hysterectomies performed in the U.S. Further, it has been estimated that 25-50% of women of reproductive age have one or more uterine fibroids, and the incidence is as much as 9 times higher in black women than in white women. Depending on the size, number and location of the fibroids, symptoms can be severe, and often include excessive or persistent menorrhagia, pelvic pain and cramping, pressure, urinary problems, constipation, anemia, or infertility. Another concern is the degeneration of fibroids to malignant leiomyosarcomas, at an incidence rate of approximately 0.5%.

FIGS. 1A and 1B are anatomical sketches contrasting a healthy patient 10 having a normal uterus 22 with a second patient 12 having a uterus showing growth of uterine fibroids in various regions. Fibroids are nodules of well-differentiated smooth muscle encased in fibrous tissue that grow in or on the wall of the uterus, with some reports of myomas demonstrating skeletal muscle differentiation. Fibroids range in size from approximately 0.5 cm to greater than 10 cm in diameter, and may grow as submucosal fibroids 30 just beneath the endometrium 14 (submucous), as intramural fibroids 36 within the myometrium 16 (intramural), or subserosal fibroids 28 beneath the serosa. They may also be pedunculated, and reside either within the uterine cavity 22 (pedunculated submucosal fibroids 34), or outside the uterus 22 in the pelvic cavity (pedunculated subserosal fibroids 32).

Treatment options for women considering bearing children are limited. The most common and permanent treatment for uterine fibroids is surgical removal of the uterus (hysterectomy), particularly in women approaching menopause. Although a permanent solution for fibroids, hysterectomy is a major surgical procedure associated with significant risk of mortality/morbidity including fever, wound infection, excessive blood loss, increased risk for transfusion, and trauma to the bladder and surrounding tissues. Recent improvements in hysterectomies performed using a vaginal approach have demonstrated reductions in blood loss, post-op complications, length of hospital stay, and overall cost. However, vaginal hysterectomies are not recommended for patients presenting with a large fibroid uterus.

For pre-menopausal women wishing to retain their uterus for reproductive, psychological or hormonal reasons, myomectomy (surgical removal of fibroids) can be a less invasive alternative to hysterectomy. The procedure may be performed via open laparotomy, or via a number of advanced laparoscopic and hysteroscopic surgical techniques. For women considering childbearing, preferred surgery is the open myomectomy in order to preserve the structural integrity of the uterine wall—the ability to apply multiple layers of suturing is severely limited for laparoscopic procedures. While complications are similar to those of hysterectomy, the complication rate is reduced from 25% to as low as 14.8%, and fertility may be improved, with pregnancy rates reported as high as 74%. However, the incidence of post-operative adhesions may be as high as 89%, and the risk of recurring fibroids requiring additional surgery or hysterectomy is 15-25%.

Hormonal therapies such as gonadotrophin releasing hormone (GnRH) agonists can be used to induce artificial menopause resulting in a 30-40% decrease in fibroid size, and a 40-50% reduction in uterine volume. The side effects experienced with hormonal therapies are similar to symptoms often associated with menopause (hot flashes, irregular vaginal bleeding, vaginal dryness, headaches, and depression). However, prolonged use may result in excessive bone loss, and the fibroids will return to their pre-treatment volumes within 3 months if treatment is discontinued. Rather than a long term treatment option, hormonal therapies are often used prior to myomectomy to reduce the size of the uterus and the fibroids thus facilitating the surgical procedure.

Uterine artery embolization (UAE) is a minimally-invasive surgical procedure used to treat fibroids by obstructing their blood supply. A catheter, advanced into the uterine artery under fluoroscopic guidance, is used to inject polyvinyl alcohol particles resulting in immediate obstruction of blood flow. Clinical studies indicate that UAE reduces fibroid volume by approximately 35-60%, and has been effective in 85% of the patients. Complications of the procedure include risk of allergic reaction to medications, infection, contrast-induced renal failure, uterine perforation, sexual dysfunction, and post-procedure pain attributed to the ischemic necrosis. Fibroid sloughing requiring additional surgery occurs in about 10% of the patients.

Laparoscopic myoma coagulation (myolysis) is a minimally-invasive procedure in which a laser or a radiofrequency (RF) needle is used to thermally coagulate and necrose uterine fibroids and their vascular supply. Both modalities can be used to thermally coagulate and reduce the size of uterine fibroids by as much as 40 to 50%. However, a recent clinical study using an RF needle electrode with extendible secondary electrodes to treat large fibroids demonstrated the ability to produce a 5 cm diameter region of necrosis resulting in as much a 77% reduction in fibroid volume. Yet spatial control of the pattern is very difficult, if not impossible. An advantage of myolysis performed using a laser fiber is that treatment can be guided and monitored in real time with MR thermal monitoring techniques. However, since the propagation of energy, and hence coagulation of tissue, is limited to a radial distance of less than 1 cm from the applicator at a single puncture, high power levels, multiple punctures (sometimes >50) and longer treatment times are often required to treat commonly occurring large myomas (5+ cm diameter) using either RF or laser modality. Techniques using either sequential insertions or multiple, simultaneously implanted laser fibers around the circumference of the fibroid have been used to coagulate the outer boundary, thus destroying the blood supply and shrinking the fibroid. Although major complications with this technique are rare, the risk of post-operative adhesions increases with the greater number of device insertions required to heat larger fibroids. Control of thermal coagulation with these technologies is determined by applied power only, with no dynamic angular or longitudinal spatial control of heating along the length of the applicator, or radially/angularly from it.

The feasibility of using cryotherapy for treatment of fibroids has been investigated. Initial studies demonstrated an overall reduction in fibroid size of only 10%; recent studies have shown clinical results similar to those obtained by other minimally-invasive treatments with mean volume reductions up to 65%. Furthermore, this technology can be used with interventional MR imaging for visualization and guidance of the cryoneedles, and monitoring of the freezing procedure. Control of the freezing zone is problematic. Complications of this technique are similar to those associated with thermal coagulation methods. The applicator diameters range 3-5 mm, and are introduced with trocars and introducer sheaths similar to our proposed procedure.

In some, the above thermal techniques (e.g. cryotherapy or high-temperature thermal ablation) have at least one of the following limitations: inability to spatially control the distribution of energy output to conform to the fibroid volume, inadequate single treatment volumes requiring multiple device insertions (increases risk of adhesions), long procedural times, or limited use due to proximity of critical tissue structures (e.g., bladder, bowel). These limitations may reduce their effectiveness and overall applicability to consistently and safely treat symptomatic fibroids.

High-intensity externally-focused ultrasound (HIFU) is a another, non-invasive method used to generate well-localized thermal damage deep within the body, while possibly avoiding damage to the overlaying or surrounding tissues. Although this technique is non-invasive and capable of precise coagulation of tissue, long treatment times (>2 hours) are required to treat small tissue volumes (12 $cm^3$), access to fibroids located in proximity to bowel or bladder is limited, and lack of adequate acoustic window and pre-focal heating limits this technology to accessible small fibroids. Significant reported complications include thermal damage or burns in deep tissue, bowel, and superficial tissue layers, including the skin beneath the acoustic interface.

There is a substantial clinical need for a minimally-invasive alternative to traditional open surgical approaches with the promise of less morbidity and recovery time, faster procedure time, and lower cost. Interstitial ultrasound has potential to provide a superior minimally-invasive heating technique for the laparoscopic treatment of uterine fibroids with the promise of more precise and thorough targeting, accessibility to a larger number of fibroids, faster procedure times, and repeatable performance acceptable to the gynecological surgeon.

BRIEF SUMMARY OF THE INVENTION

The present invention may be used to treat fibroids, including ones considered too large for existing heating technologies, by using ultrasound energy to heat or ablate the fibroid or a portion of the fibroid. The ultrasound system and methods of the present invention allow directional control and deep penetration of energy patterns for directed thermal arterial occlusion/coagulation. With the system of the present invention, large fibroids can be treated by targeting a smaller portion of the tumor with the feeding vasculature, thus reducing the treatment time and improving chances for complete regression. In addition, this requires less of a volume be thermally fixed or destroyed, which may remain in the body for some time and in some circles considered clinically undesirable.

The present invention is directed to a high-power intracavitary and interstitial ultrasound heating applicators for minimally-invasive thermal ablation of uterine fibroids or myomas. High-intensity intracavitary and interstitial ultrasound, applied with minimally-invasive laparoscopic or hysteroscopic procedures, is used to effectively treat fibroids within the myometrium in lieu of major surgery, providing a better alternative treatment for women wishing to bear children. The applicators of the present invention are configured with high-power capabilities and thermal penetration to treat large volumes of fibroid tissue (>70 $cm^3$) in short treatment times (3-20 minutes), while maintaining three-dimensional control of energy delivery to thermally destroy the target volume. Directional or selective heating may be used as a means of preserving surrounding healthy tissue, for example to avoid bladder, bowel or other sensitive organs.

An aspect of the invention is an apparatus for treating uterine fibroids, having a catheter with a distal end and a proximal end and an ultrasound applicator disposed at the distal end of the catheter. The applicator has one or more transducers disposed longitudinally along a central axis of the catheter, wherein the one or more transducers are coupled to a power source external to the catheter. In particular, the ultrasound applicator is configured to be positioned to a treatment location at or near a fibroid tissue mass and deliver high-intensity ultrasound energy sufficient to heat and destroy the fibroid tissue mass. The delivered energy is sufficient to ablate or necrose the fibroid tissue.

In a preferred embodiment, the applicator is configured such that sufficient energy is applied to treat the fibroid tissue within a period ranging between approximately 3 to 20 minutes, and preferably 5 to 15 minutes.

The applicator ideally comprises an array of two to five transducers, and more preferably three to four transducers. In one embodiment, the transducers are tubular and disposed adjacent each other over a support element in a linear array.

In another embodiment, the transducers are configured to provide directional energy distribution of the ultrasound energy in a first direction associated with the fibroid while shielding ultrasound energy in a second direction. The transducers may be configured to emit ultrasound energy in a substantially 360° pattern radially from the axis of the catheter, or emit a radial pattern less than 360°, e.g. 180°, 120°, or 90°, etc. In addition, the transducers may be sectored and individually wired to each emit a portion of a 360° radial pattern. Additionally, the transducers may be each arcuate and emit focused energy as a line focus in a specific direction pointing into the fibroid, which may be selected by rotating the transducer.

The ultrasound transducers may be disposed within the catheter, (e.g. emit through the catheter walls, or be disposed adjacent to the distal end of the catheter.

The catheter may also be configured to provide fluid cooling to the ultrasound elements. In one embodiment, the applicator further comprises a balloon emanating at the distal end of the catheter, wherein the balloon configured to surround the one or more transducers to circulate the cooling fluid around the one or more transducers. The catheter may also comprise a multi-lumen catheter with a first lumen configured to deliver fluid to the applicator, and a second lumen configured to transport fluid out of the applicator.

The device may also comprise a retractable sheath configured to surround the applicator during delivery to the treatment site.

In another embodiment, the device includes a temperature probe disposed at the distal end of the catheter, wherein the temperature probe is configured to acquire temperature readings at one or more locations of tissue in vicinity to the applicator.

In yet another embodiment, the catheter comprises a bendable portion proximal to the applicator such that the applicator may be oriented at an angle with respect to the catheter proximal to the bendable portion, wherein the bendable portion comprises a material configured to retain the angle as the applicator is delivered to the treatment site.

The applicator may be configured to be delivered via laparoscopic access, hysteroscopic access, or both.

Another aspect of the invention is a method of treating a uterine fibroid. The method includes the steps of positioning an ultrasound transducer at a treatment location at or near a fibroid tissue mass, and administering power to the transducer to deliver high-intensity ultrasound energy to the fibroid tissue mass sufficient to heat and destroy the fibroid tissue mass, e.g. via ablating or necrosing the fibroid tissue.

Prior to delivery of the ultrasound energy, the power, treatment time, and frequency of the ultrasound energy may be determined based on the fibroid tissue anatomy, and input into a computer controlling the energy transmitted from the transducer.

In one embodiment, the ultrasound energy is delivery to only a portion of the fibroid tissue, ideally the portion comprising feeding vasculature.

In another embodiment, a thermal sensor may be deployed to obtain temperature feedback of tissue at or near the applicator. Also, the method may include determining the extent of arterial occlusion by applying one or more of the following diagnostic techniques: such as fluoroscopic, Doppler ultrasound, MRI, or CT imaging.

The energy may be delivered from the applicator in an array of transducers. In some embodiments, the transducers are individually operable to independently or concurrently deliver ultrasound energy.

In one embodiment, the applicator is delivered to a substantially central location within the fibroid tissue, and is controlled to emit ultrasound energy in a substantially 360° pattern radially from an axis of the catheter.

Alternatively, the applicator is delivered to a location substantially adjacent the fibroid tissue, and controlled to emit ultrasound energy in a radial pattern less than 360°, e.g. a radial pattern of approximately 180° or less.

In another embodiment, the method may include delivering a cooling fluid to the applicator through the catheter during delivery of ultrasound energy.

Another aspect of the invention is an apparatus for treating uterine fibroids, having a catheter with a distal end and a proximal end, and an ultrasound applicator disposed at the distal end of the catheter. One or more tubular or arcuate transducers are disposed longitudinally over a support element that is substantially coincidental with a central axis of the catheter. A power source external to the catheter is coupled to the one or more transducers. In particular, the ultrasound applicator is configured to be positioned at a treatment location to deliver high-intensity ultrasound energy sufficient to heat and destroy a fibroid tissue mass located at or near the treatment location.

In one embodiment of the current aspect, the applicator comprises an array of two to five transducers disposed adjacent each other in a longitudinal array, and preferably an array of three to four transducers.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 3 further illustrates the laparoscopic procedure with the ultrasound applicator of the present invention positioned adjacent the target fibroid.

FIG. 4 shows a hysteroscopic procedure in accordance with the present invention.

FIG. 5 shows a distal tip of a conformable ultrasound applicator of the present invention.

Figure 6:
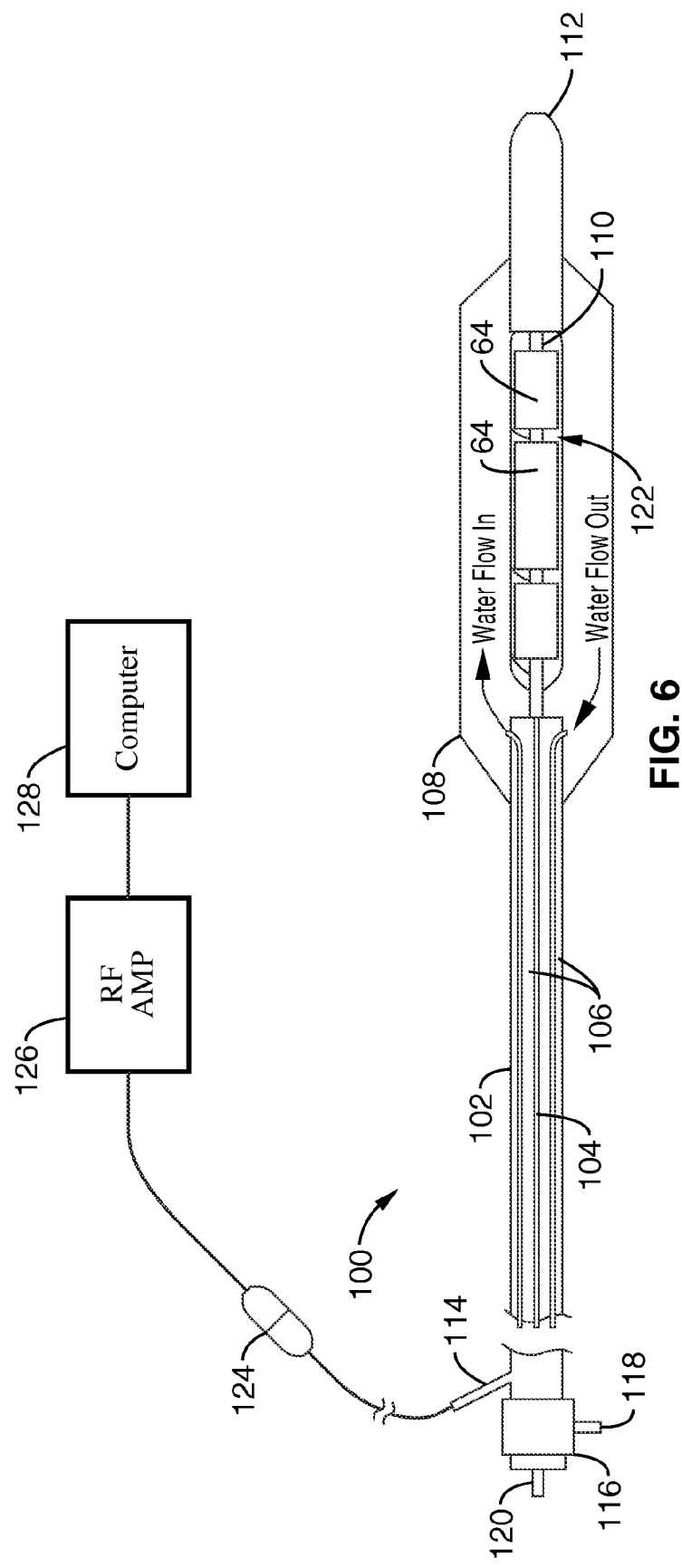

FIG. 6 illustrates a liquid-cooled applicator.

FIGS. 7A-7D illustrate side views of various ultrasound element configurations.

Figure 8:
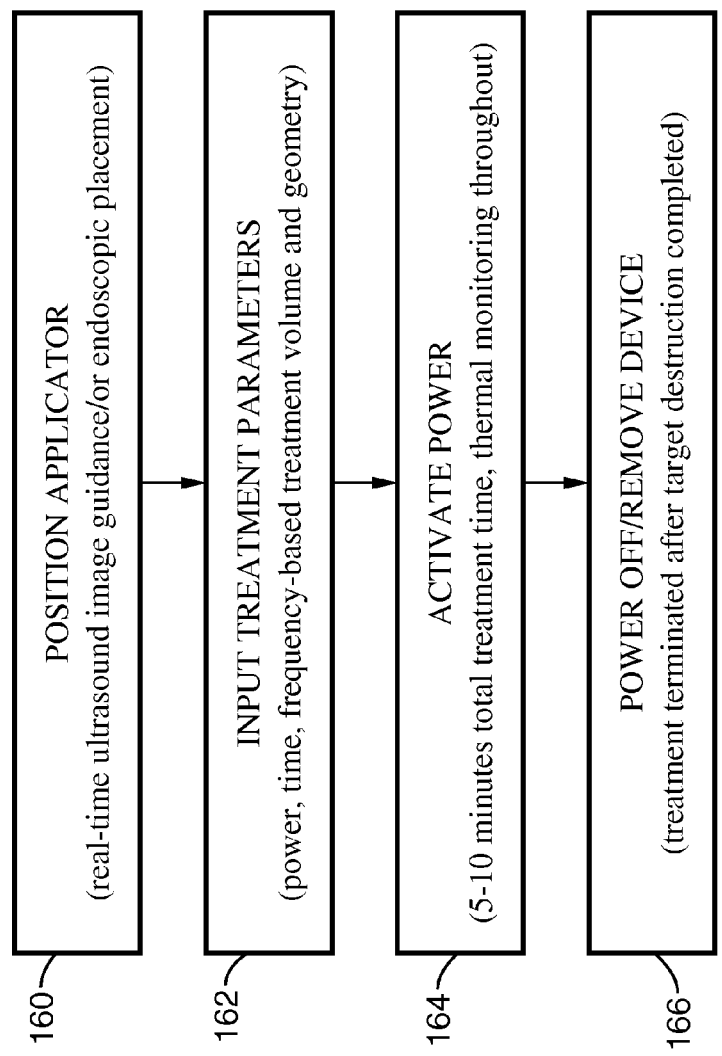

FIG. 8 illustrates a flow diagram of an exemplary fibroid treatment process in accordance with the present invention.

Figure 9:
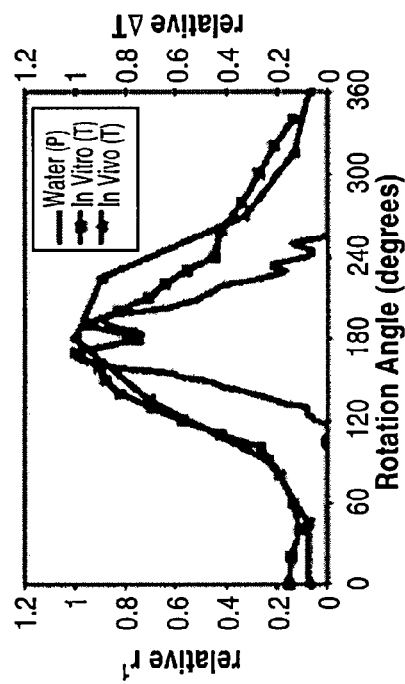

FIG. 9 illustrates angular and axial control of power deposition ($P^2$) and heating from in vivo measurements of temperature and zones of thermal coagulation.

Figure 10:
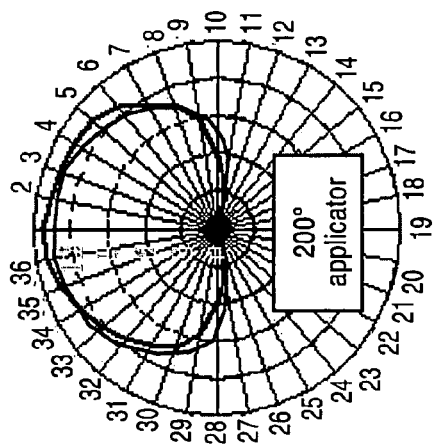

FIG. 10 shows a plot of ultrasound energy distribution of a 200 degree applicator.

Figure 11:
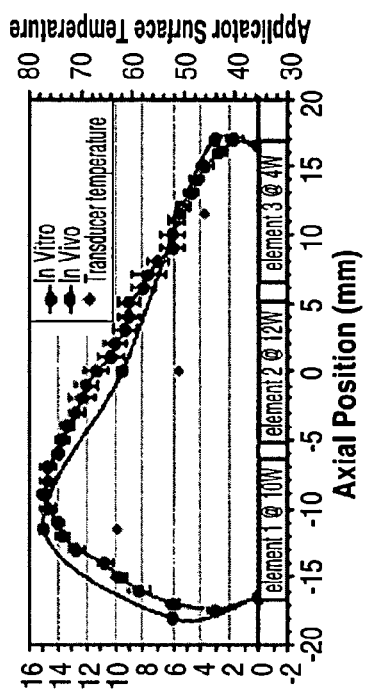

FIG. 11 is a graph of the treatment depth across the axial position of the applicator.

Figure 12C:
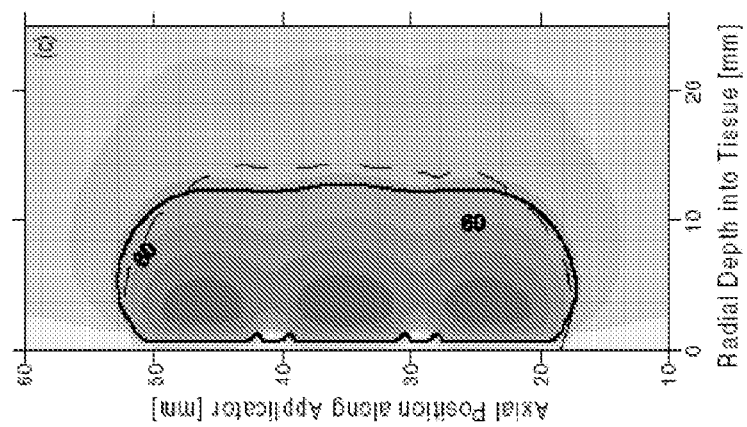
Figure 12B:
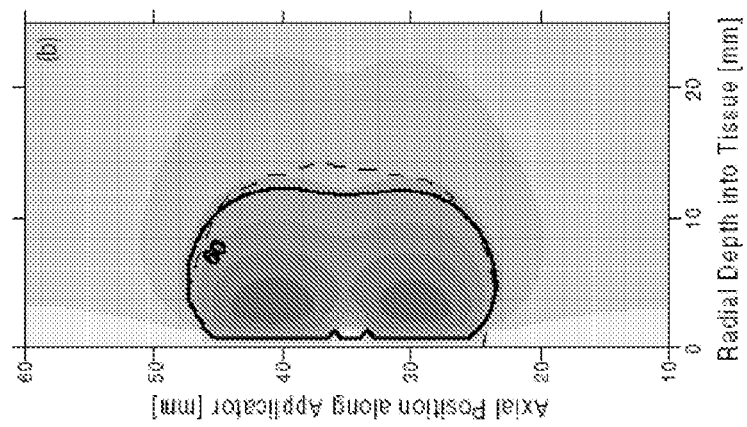
Figure 12A:
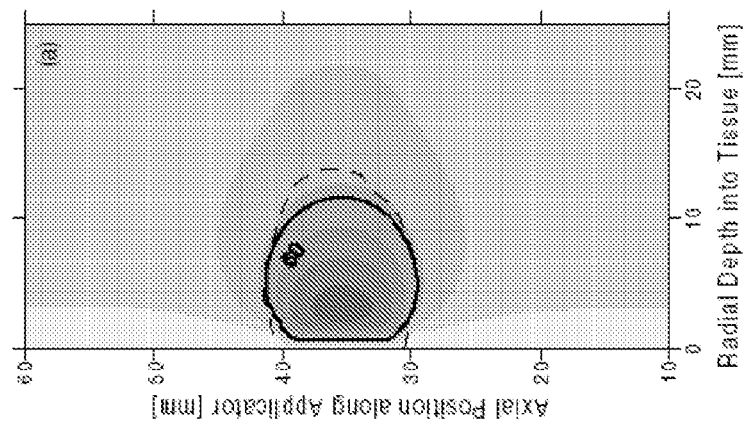

FIGS. 12A-12C show a simulation of the radial depth into tissue for one, two, and three element applicators.

Figure 13:
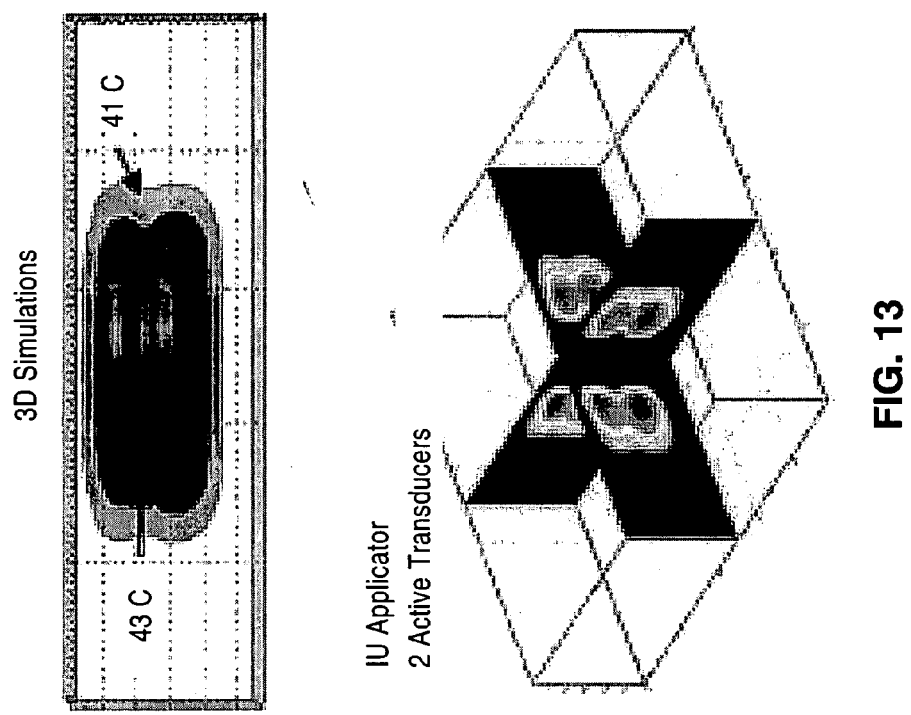

FIG. 13 illustrates the 3-D distribution of a 2-transducer applicator.

Figure 14:
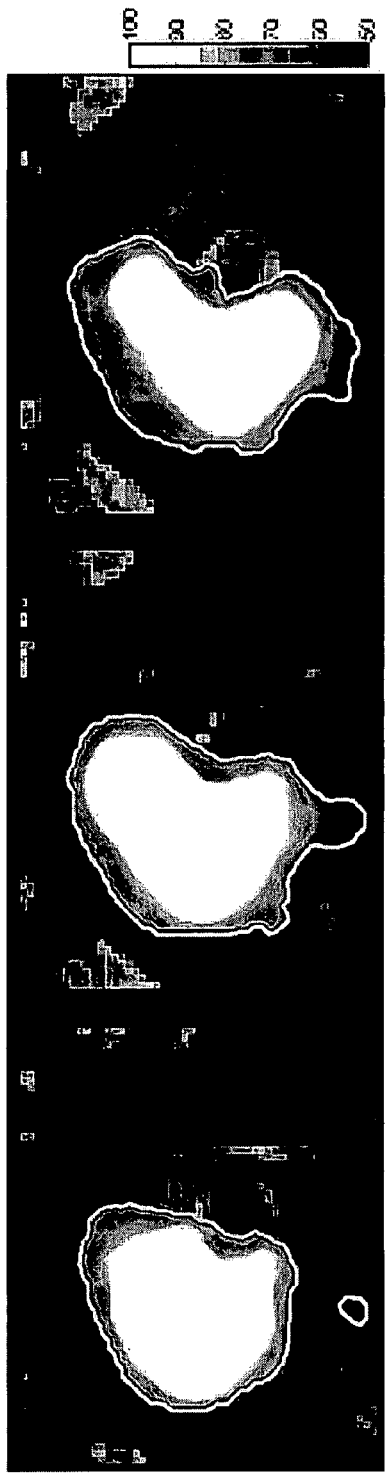

FIG. 14 illustrates MRI images of the thermal dose delivered to tissue during application.

Figure 15:
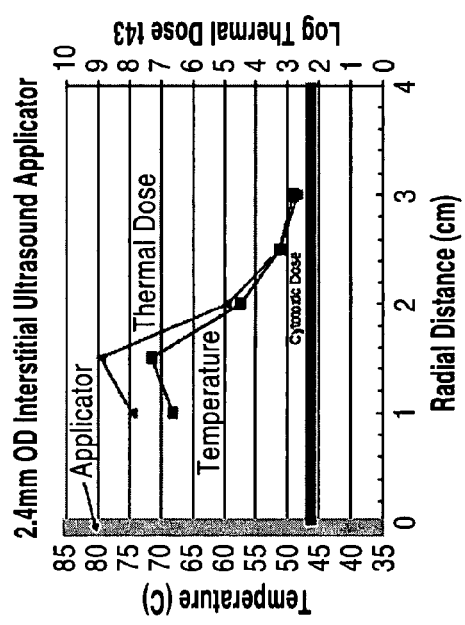

FIG. 15 illustrates test results for temperature and thermal dose measurements of a 2.4 mm OD ultrasound applicator.

Figure 16:
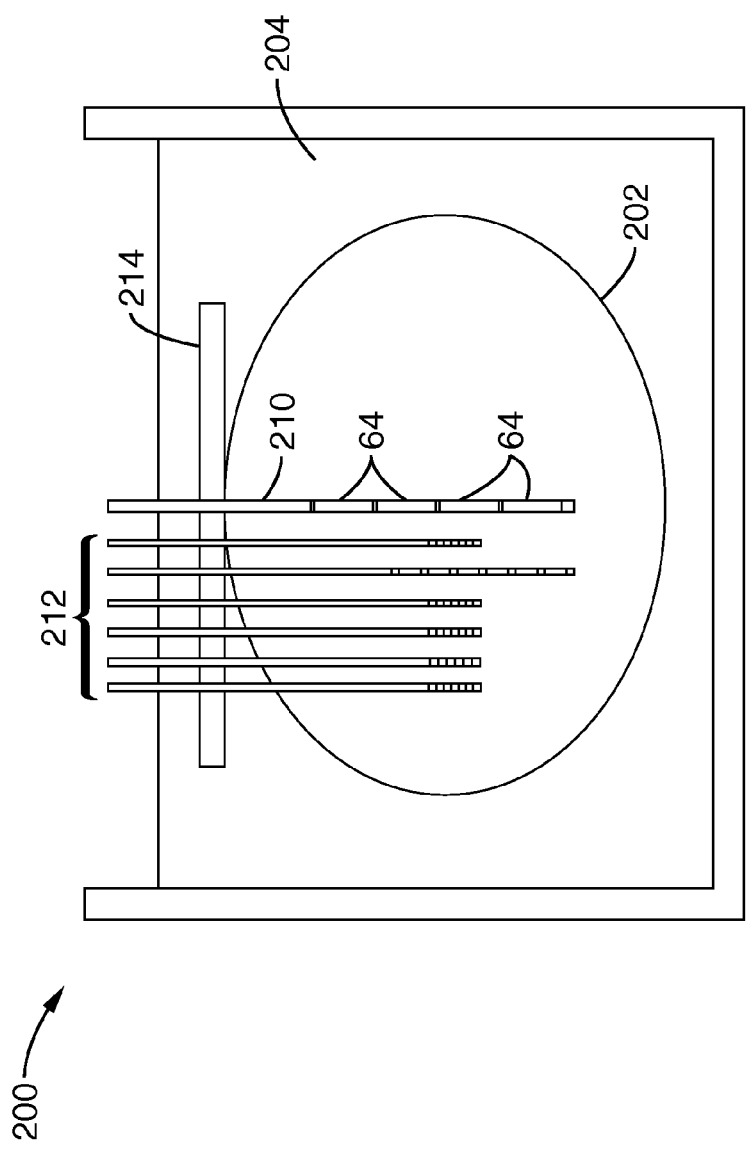

FIG. 16 illustrates an exemplary test set up for testing the ultrasound applicator of the present invention on an ex-vivo human fibroid sample.

Figure 17:
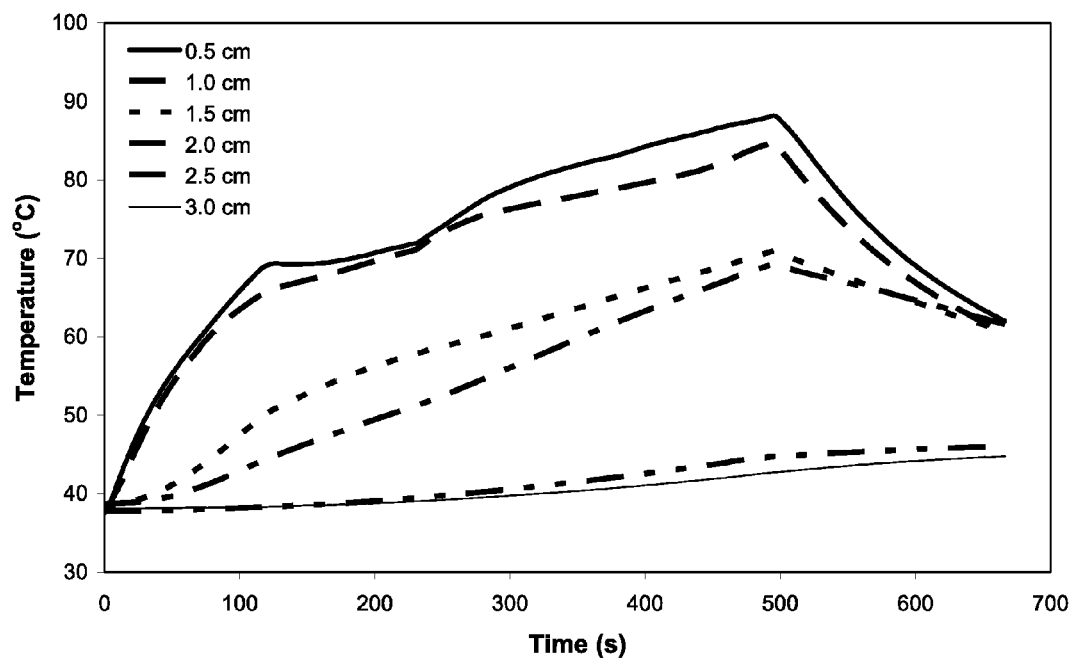
Figure 18:
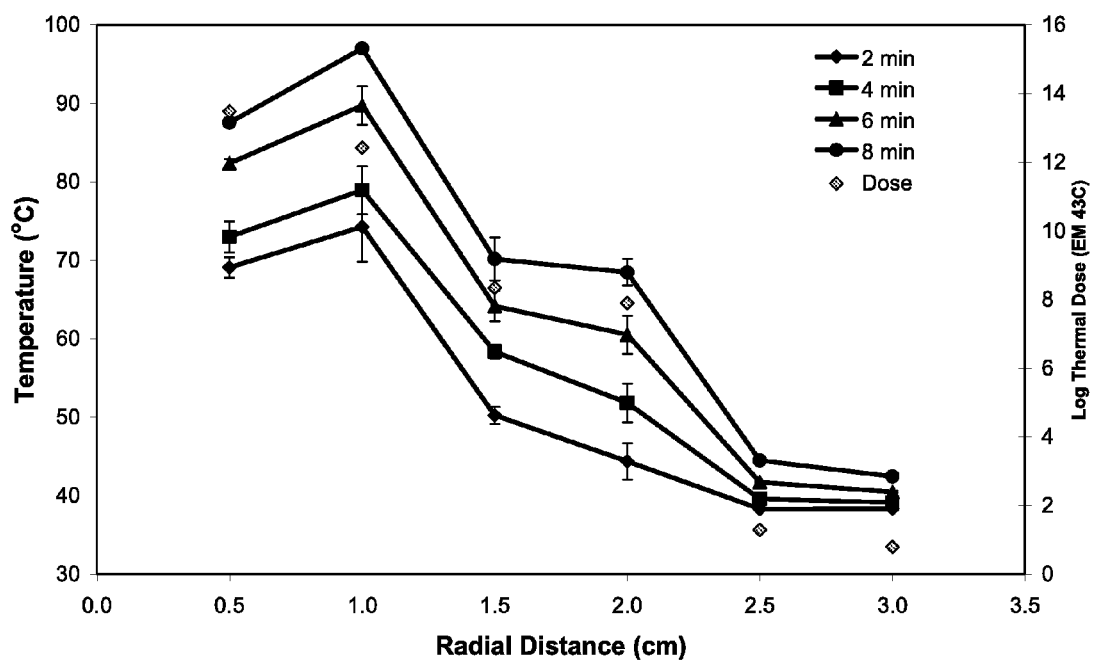
Figure 19:
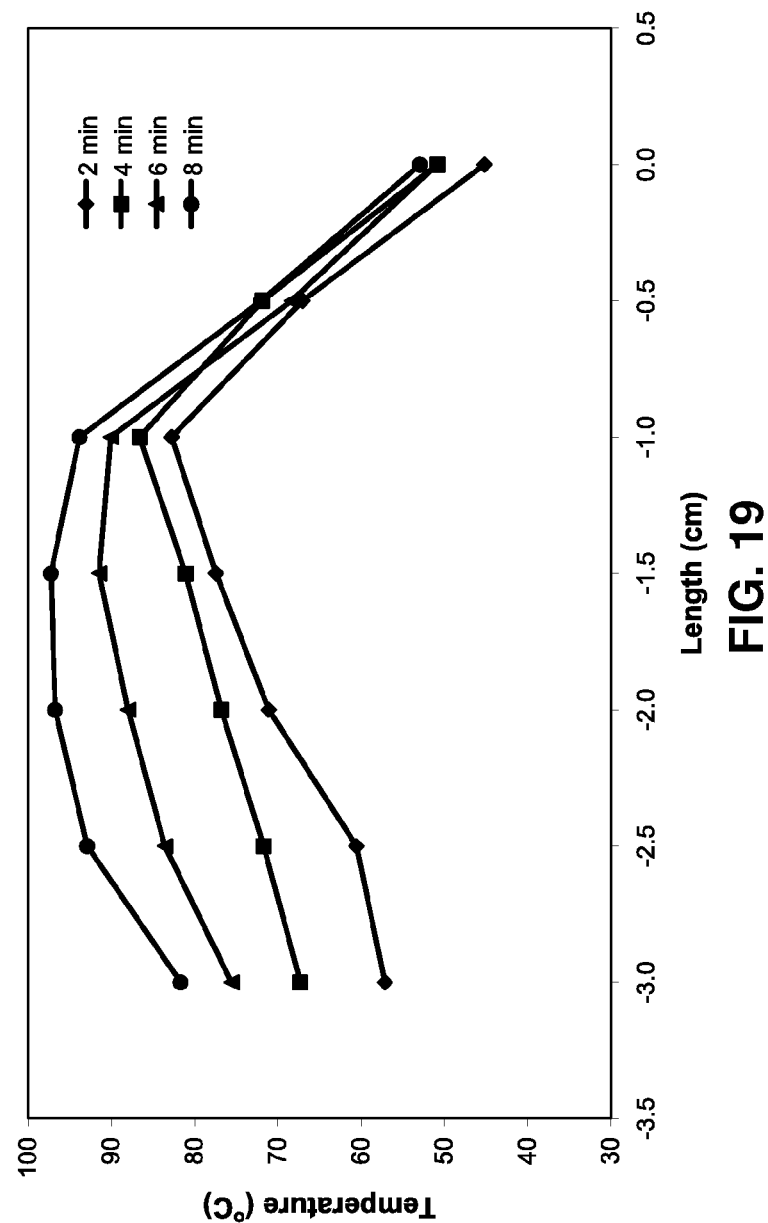

FIGS. 17-19 illustrate the results of the heating trial in a human uterine fibroid using a 4-element applicator with 360 degree heating pattern inserted in a 13 g catheter with 60 ml/min flow rate.

Figure 20:

FIG. 20 illustrates a sagittal slice through thermal lesion, visualized after 20 minutes in a 2% TTC solution.

Figure 22:
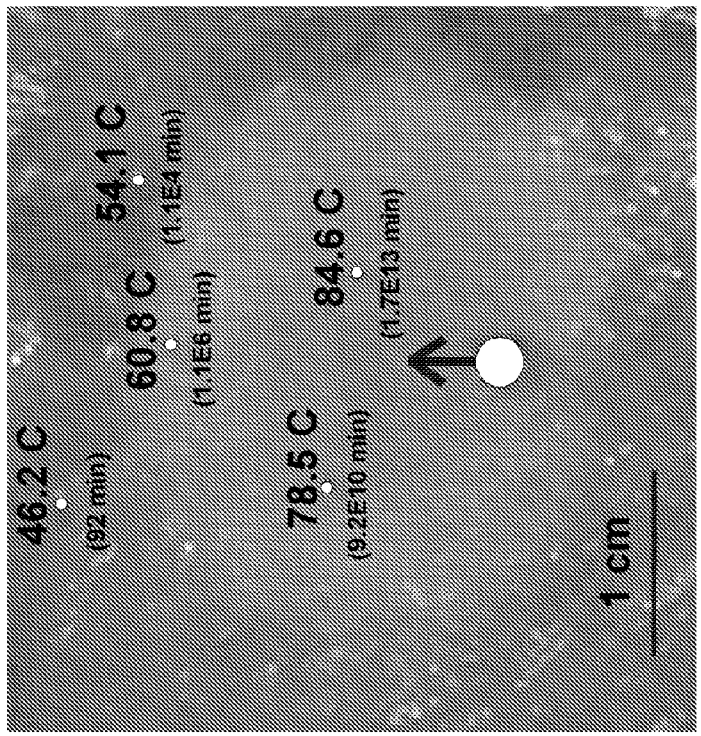
Figure 21:
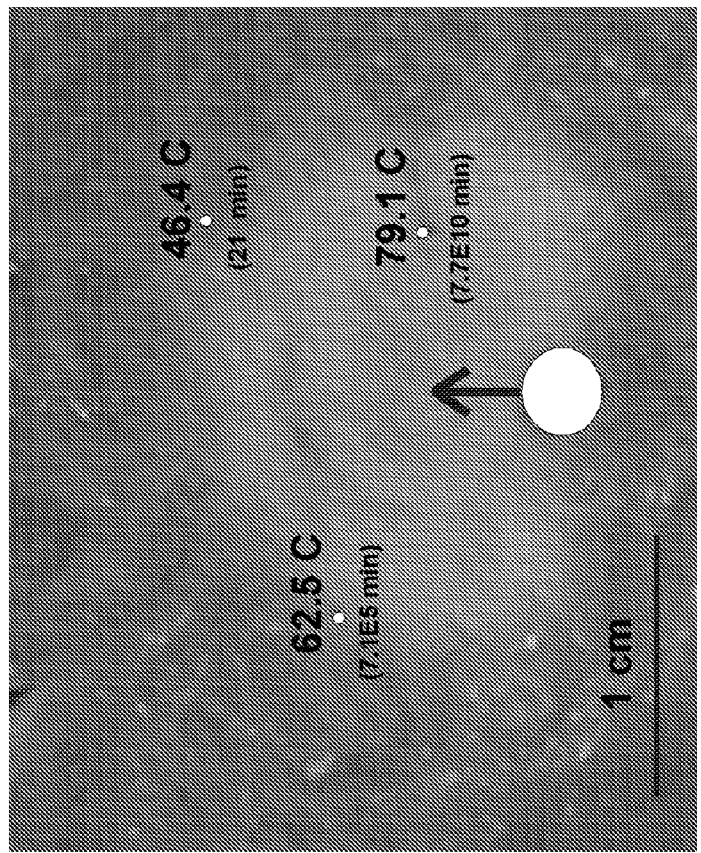

FIGS. 21 and 22 illustrate transverse slices through thermal lesions (as visualized using TTC stain) generated in human uterine fibroids using a 3-element applicator with a 180 degree directional heating pattern, inserted in a 3.7 mm OD catheter with 60 ml/min flow rate.

Figure 23:
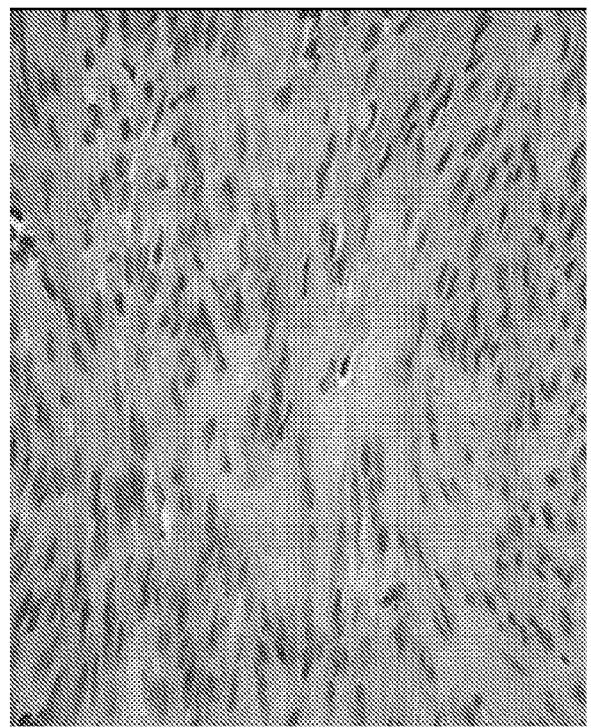

FIG. 23 illustrates untreated tissue showing lighter, heterogeneous and slightly granular chromatin, and visible nuclear features.

Figure 24:
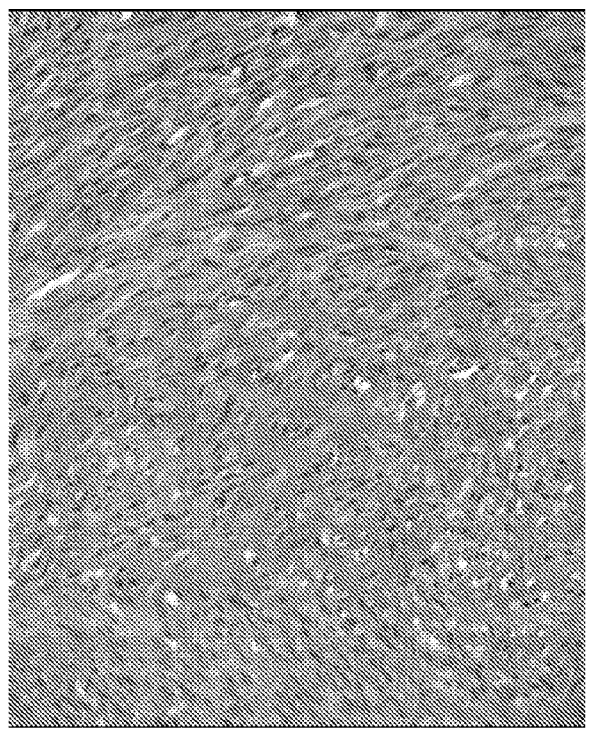

FIG. 24 shows treated tissue indicating hyperchromatic nuclei.

Figure 25:
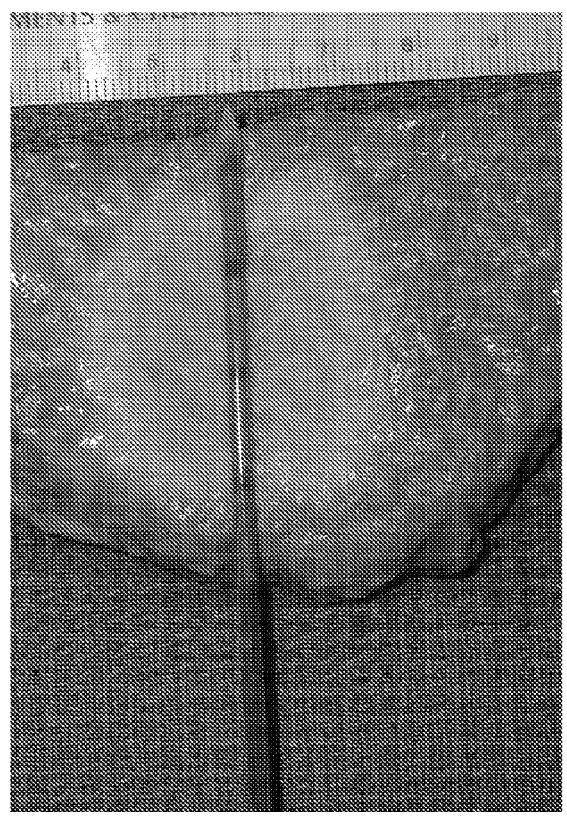

FIG. 25 illustrates a three×10 mm transducer applicator and resulting tissue lesion.

Figure 26:

FIG. 26 illustrates a four×10 mm transducer applicator and resulting tissue lesion.

Figure 27:
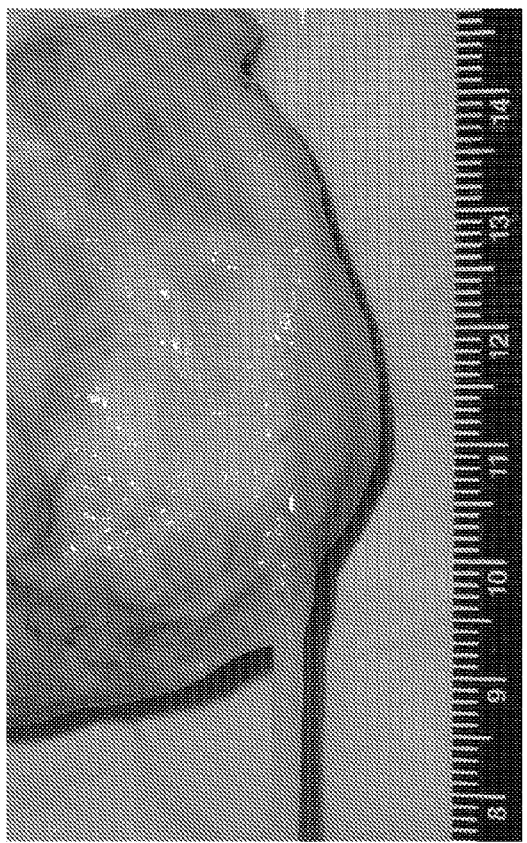

FIG. 27 illustrates a lesion created by a two×10 mm transducer applicator with 180° directional distribution.

Figure 28:
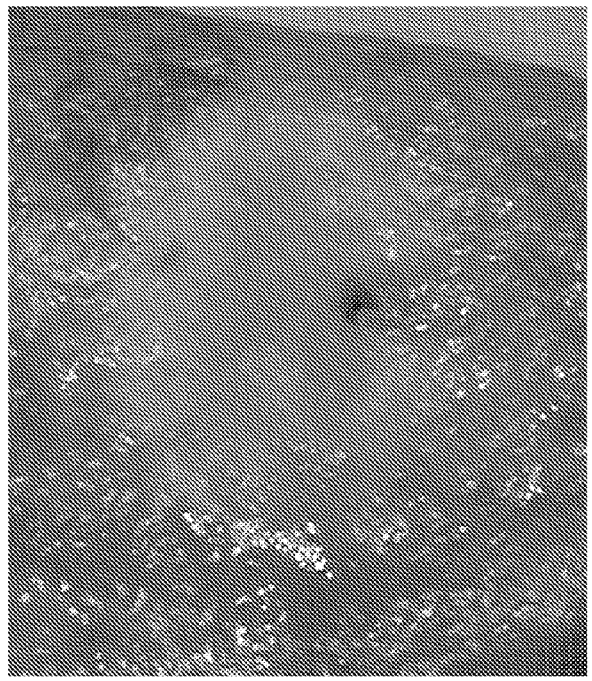

FIG. 28 illustrates a lesion created by a 180° directional distribution applicator and insertion point.

DETAILED DESCRIPTION OF THE INVENTION

Referring more specifically to the drawings, for illustrative purposes the present invention is embodied in the apparatus and method generally shown in FIG. 2 through FIG. 28. It will be appreciated that the apparatus may vary as to configuration and as to details of the parts, and that the method may vary as to the specific steps and sequence, without departing from the basic concepts as disclosed herein.

Figure 1A:
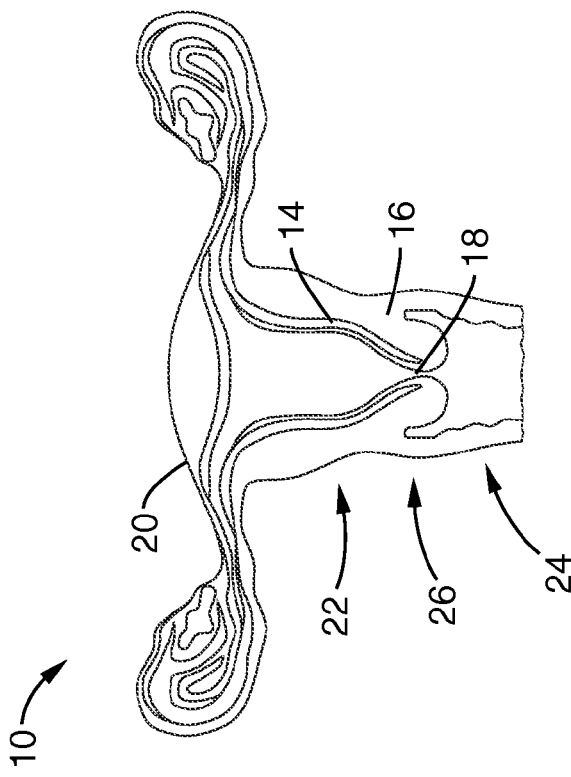
FIG. 1A is a diagram of a healthy uterus.
Figure 1B:
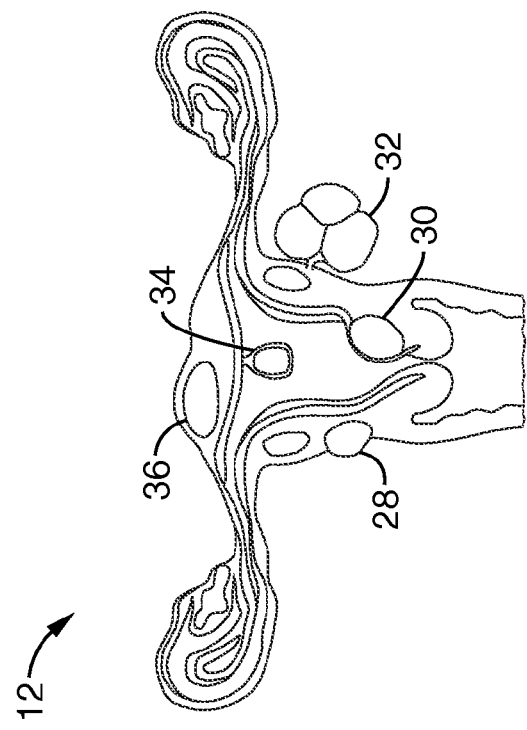
FIG. 1B is a diagram of a uterus with fibroids.
Figure 2:
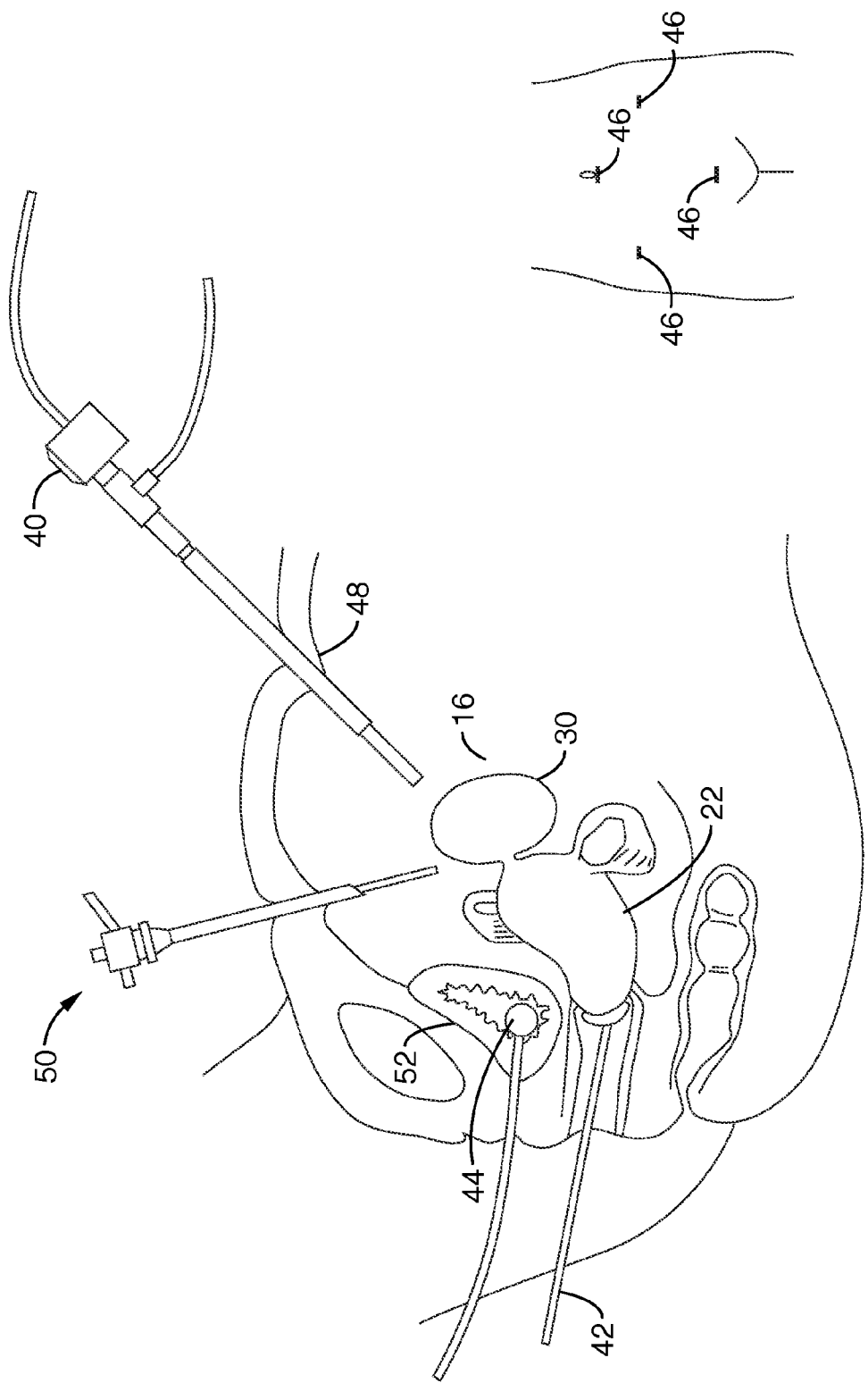
FIG. 2 illustrates a laparoscopic approach to treating fibroids in accordance with the present invention.

FIG. 2 illustrates the overall schema for laparoscopic interstitial ultrasound thermal treatment of a uterine fibroid 30 embedded in myometrium 16, following procedures similar to those used for laparoscopic myomectomy or recent RF/cryotherapy ablation studies, providing a simple and minimally-invasive treatment technique.

Multiple access ports 46 (generally three to five) for the laparoscope 40 and surgical instrumentation (e.g. catheter 44) may be placed within the abdominal wall 48, and the abdominal cavity pressurized with gas. The uterus 22 may be positioned with a standard manipulator 42 and a path to the fibroid 30 cleared.

The ultrasound applicator 50 may be centered or placed eccentric within fibroid 30 using standard manipulators to position tissues prior to insertion. Positioning of applicator 50 to the treatment site may be affected via a working channel of laparoscope 40, or via a dedicated port as shown in FIG. 2.

Pre-operative imaging studies, direct magnified visualization, and/or the use of intraoperative ultrasound imaging can be used to determine treatment parameters a priori and verify device placement, with Doppler ultrasound able to localize feeding vasculature for targeting.

Referring to FIG. 3, the ultrasound therapy device 50 of the present invention is configured for insertion directly into the fibroid 30 during laparoscopic surgery. The device 50 may comprise a rigid introducer sheath 62 configured to be inserted into the fibroid 30. The device 50 may also comprise thermometry sensors 66 that deployable within the target volume of the fibroid 30. The sheath 62 may be retracted once the high-powered ultrasound applicator 50 is inserted to a predetermined depth.

The applicator 50 of the present invention includes substantial power output (30-50 W/cm$^2$ applied power) with controlled heating of larger tumor volumes.

High-powered ultrasound may be applied via one or more ultrasound transducers 64 positioned at the distal tip of the applicator 50, and may be applied at preset power levels and duration to conform therapy to the target zone 70 for the thermal lesion. Applicator transducers 64 may be at least one of the following: tubular, planar, or arcuate. The applicator 50 preferably includes a deployable pre-shaped thermocouple temperature probe 66 (e.g. nitinol hypodermic tubing, pre-shaped by heat fixation) that is integrated with the introducer sheath 62 and designed to deploy into the target zone 70. Deployable temperature sensing via sensor array 66 provides treatment verification and feedback so that only the desired treatment region or target zone is affected. Furthermore, additional protection can be instituted by placing a small air-gap or acoustic blocking or shielding material 68 between the applicator and the area to be protected (e.g. bowel 72 or bladder 52).

As shown in FIG. 4, applicator 80 may be configured to deliver treatment hysteroscopically via vaginal access 24 into uterus 22. Applicator 80 may be configured and shaped specifically for this type of procedure, or may be configured to be used interchangeably for laparoscopy or hysteroscopy.

FIG. 5 illustrates an ultrasound applicator 90 configured to be compliant to bend at a point proximal to distal tip 92 and the applicator elements 64. In this configuration, the applicator may comprise a compliant memory material (e.g. nitinol) at location 96 so that the distal tip 92 may be bent at an angle θ with respect to proximal section 94 as desired by the physician according to the anatomy of the patient and location of the fibroid, and retain its shape throughout the procedure. In an alternative configuration (not shown), the applicator tip 92 may be steerable by inclusion of one or more guidewires extending from the proximal end of the catheter to the distal tip. Thus, the applicator tip may be bent to the desired shape while the applicator is positioned at the treatment location within the patient's body by pulling on the guidewire.

The applicator 50, 80, 90 is preferably configured to withstand the rigors of laparoscopic surgery, and have support systems and control, manipulators and procedures, specific tooling, treatment feedback and control schemes, and treatment planning schemes based upon pre-operative and/or intra-operative imaging studies, treatment modeling, on-line real-time thermal dose monitoring/control.

FIG. 6 illustrates a high intensity catheter-cooled interstitial ultrasound applicator 100 of the present invention. A plurality of transducers 64 are positioned at or near the distal tip 112 of a multi-lumen catheter 102. The number of transducers may vary from 1 to over 5, but preferably range from 2-4 transducers. The transducers are generally cylindrical or tubular members that fit sequentially over polymide support tube 110. Each of the transducers may be separated by a coating 122, which may comprise, for example, a lamination of an epoxy, silicone adhesive and polyester layers or combination of the above. Other layering/materials may be also be used as desired.

Catheter 102 preferably comprises inbound and outbound lumens 106 (e.g. multi-lumen catheter) for cooling water flow 106. The cooling liquid (e.g. water) may be cycled at and around the transducers 64 via inlet port 120 and outlet port 118 at proximal end 116 of the catheter. The cooling liquid may be cycled within a polyester balloon 108 to achieve active water-cooling of the transducer crystals 64. RF power lines 104 may be feed out port 114 for quick-connect leads 124 or like connection.

The applicators 50, 100 may be configured in three primary size configurations: 1) smaller applicators with a 14-15 g needle/catheter (1.8-2.1 mm OD), 2) larger diameter devices utilizing 8-9 g catheters (3.8-4.2 mm OD) (e.g. placed through a laparoscope 40 working channel), and 3) revision of a 2.4 mm diameter 13 g device to increase power handling. The smaller 14-15 g catheters generally represent a lower size limit for applicators with the proposed high powers, and can be used with existing instrumentation for laparoscopic and hysteroscopic approaches. Though these smaller sizes are preferred for insertion, the two larger devices may be beneficial for attaining maximum power handling capability, and can be used with larger trocars and modified approaches for laparoscopic, and hysteroscopic insertion (similar sizes are currently used clinically for cryotherapy probes).

Fabrication of the applicators may be achieved with use of tubular piezoceramic ultrasound transducers 64 located around polymide tubing 100 (see FIG. 6), with an operating frequency of approximately 7 MHz.

For achieving high power output, the tubular ultrasound transducers 64 may vary by the type of piezoceramic material, size of the transducer crystal, power handling capability, uniformity of wall thickness, efficiency optimization, electrical impedance, frequency, piezoelectric activity, electro-acoustic conversion efficiency, consistent power output, and robust coverings. Piezoceramic material selection may be based on maximum power handling and crystal displacement characteristics, using comparisons between PZT-4 and PZT-8.

Transducer 64 diameter may be determined by the size restriction of the external catheter, using 1.0-1.5 mm OD tubular transducers for the smaller 13-15 g catheters, and larger transducers of 3.0-3.5 mm OD to maximize power output for the larger catheters. Transducer 64 lengths may range from approximately 6-20 mm, and be configured to have the appropriate balance between axial power potential and electrical impedance.

The catheter-cooled ultrasound applicator 100 may utilize Celcon (acetal copolymer) for the implant catheter 102 material. While this material has been sufficient for low to moderate power applications, it may be limited at higher powers due to acoustic properties that partially block energy transmission. Suitable catheter materials, e.g. thermoplastics such as polycarbonate, polyether (Pebax and Hytrel), nylon 6-6, polyethylene, and polypropylene, may be selected based on a number of material properties. Criteria used to select the materials may include both acoustic properties (acoustic attenuation and impedance) and thermal properties (thermal conductivity, melting temperature, and deflection temperature), as well as overall stiffness/durability of the material and its ability to be extruded, and the optimal combination of these material properties to maximize power output. The diameter and thickness of the catheter 102 material are configured for the appropriate applicator dimensions to provide a robust delivery device while minimizing blockage of energy transmission.

The cooling system, mechanisms, and flow schemes of the applicator 50 are configured to achieve levels of convective cooling necessary to allow higher levels of applied power (30-50 W/cm$^2$ applied power).

The transducers 64 may also be shaped to provide controlled and directed heating of tissue, and maintain control and directionality of tissue heating at higher power levels. Specifically, the shape may be configured to maintain longitudinal control (heating control along the length of the applicator 50) and angular control (heating around the applicator 50). Multiple transducer elements (for example, but not limited to 1-5 transducers) may be used to achieve heating lengths of 5 cm or greater, as well as to control the length of heating with individual power to each transducer element with collimated acoustic output.

The applicators may be fabricated using transducers with 360° angular acoustic output to maximize the potential treatment volume and the uniformity of circumferential heating. In this case, access to the fibroid is such that the applicator 50, 80, 90 may be positioned within a central location in the fibroid, and wherein the fibroid is not directly adjacent sensitive organs.

Figure 7B:
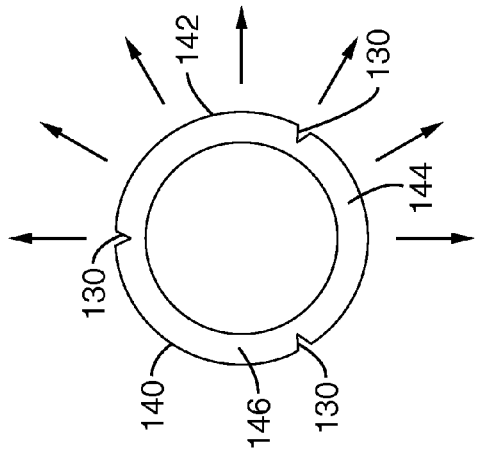
Figure 7D:
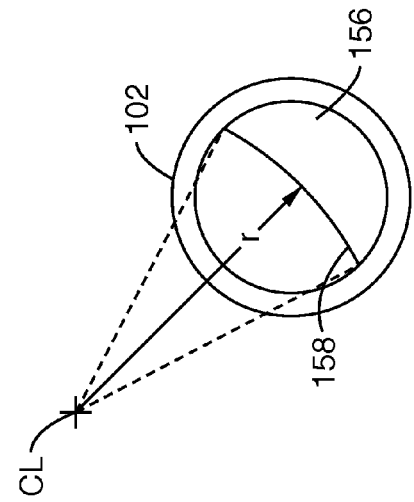
Figure 7A:
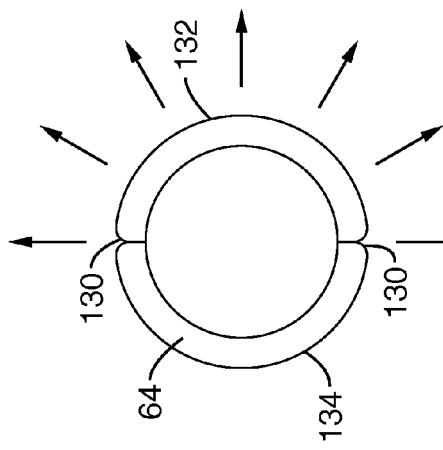
Figure 7C:
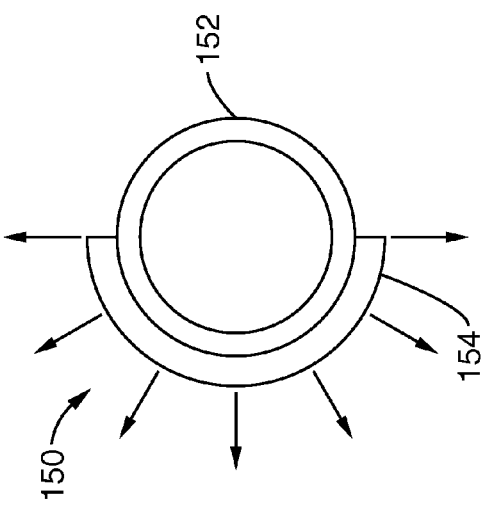

As shown in FIGS. 7A-7C, the applicators may also be fabricated using transducers that are sectored to provide a specific angular acoustic region (i.e. 60° to 180°) for placement at the periphery of a target region, selectively destroying the tissue on one side while preserving critical tissue (e.g. bladder, rectum) on the other side. This configuration is ideal where access to a central location within the fibroid 30 is not available, and to protect anatomy that is adjacent or near the fibroid 30.

FIG. 7D illustrates an example of an arcuate transducer 156 having a concave transmission surface 158 configured to produce a focal zone extending outside of the outer diameter of the catheter 102 into the tissue under treatment. The radius r of the concave surface is configured to be larger than the radius of the catheter 102 to ensure that focus CL (the focused beam path center line for the transducer along the axis of the catheter) is outside the catheter 102. The radius r may be varied so that the beam path CL focuses on a desired location away from the catheter 102. In this configuration, the applicator may be swept across a path to treat a volume of tissue. For example, the applicator may be placed adjacent a fibroid 30 outer surface with the surface 158 and beam path CL pointing inward toward the center of the fibroid. The applicator may then be swept around the fibroid outer surface to treat the entire volume of the fibroid.

As shown in FIG. 7A, element 64 may comprise two notches 130 in the surface of the element to electrically isolate a first portion (half) 132, from a second portion 134. As shown in FIG. 7A, the notches 130 are 180° apart from each other, allowing an 180° distribution pattern from side 132. Only one side may be wired (e.g. section 132) or both may be individually wired for selective and independent control of each section 132, 134.

As shown in FIG. 7B, applicator element 140 may have three or more notches 130 to have additional sections 140, 142, 144 for individual control. As shown in FIG. 7B, section 142 is configured to emit a 120° distribution beam. Each segment may be operated independently and/or concurrently, and adjusted according to different levels (e.g. power from 0 to max, frequency, and emission time) for desired coagulation or distribution.

Referring to FIG. 7C, element 150 may be configured to have electrical covering 154 etched and removed to have emitting section 154 to have a less than 360° distribution.

The general durability and robustness of the ultrasound applicator 50 are a factor of the thermal thresholds and mechanical thresholds for both transducers 64 and delivery devices.

The applicator 50 of the present invention is optimized for maximum transducer power output, electro-acoustic efficiency, and acoustic beam intensity distributions. Power may be applied to transducers using a 16-channel amplifier system (0-50 W/channel, frequency range 6-10 MHz, Advanced Surgical Systems).

For the proposed application in treating fibroids, high levels of power will be applied for approximately 5-15 minutes.

Performance criteria may include power application of 30-50 W/cm² or more for 5 minutes with at least 40% conversion efficiency, or more.

Referring back to FIG. 6, the therapy delivery system of the present invention may include a computer 128 driving a common software interface using LabView and C++ to control RF amplifiers (four or sixteen channel) 126 and a 32 channel temperature measurement system. Software functionality may include user input control of RF power and frequency control for each channel, recording forward/reflected power levels, data logging amplifier parameters, and alarms at preset reflected power thresholds. Thermometry software may include multi-sensor temperature sensing, e.g. of sensor array 66, for computing cumulative thermal dose, data logging, and color bars to indicate status of each temperature point (i.e., sublethal, lethal, max threshold). Embedded and C++ software may be used for amplifier control and temperature/dose monitoring and feedback.

FIG. 8 illustrates an exemplary flow diagram for the uterine tumor treatment process of the present invention. First, the applicator (50, 80, 100, etc) is positioned to the treatment site at step 160. Direct optical visualization using a laproscope/hysteroscope, and/or via real-time ultrasound image guidance may be used to direct the applicator toward the target region.

The treatment parameters (e.g. power, time, frequency) are then input at step 162 into the computer 128. These parameters are generally a function of the treatment volume, geometry and location of the lesion, and may be assessed with a pre-operation evaluation.

The power is then activated to the applicator at step 164. Generally, this will take approximately 5-10 minutes, and thermal monitoring may be performed throughout this step. Preferably, the energy is directed toward feeding blood vessels and maintained at the target vasculature until temperatures sufficient to collapse and/or destroy the vasculature are obtained. Thus, it may be sufficient to just heat a portion of the fibroid to obtain the desired therapeutic effect. The applicator may also be swept across a region of the fibroid 30 if needed. Temperature feedback may be obtained via the deployable thermal sensors 66. In addition, the extent of arterial occlusion or other effects of thermal therapy may be assessed non-invasively during or following heating by diagnostic techniques such as Doppler ultrasound imaging of the treated vascular region with contrast media for cases where the vasculature is targeted, fluoroscopy with contrast, MRI T1 contrast enhanced imaging, or contrast enhanced CT imaging. Other monitoring methods include acoustic harmonic motion imaging, pattern recognition analysis of backscatter image data, and acoustic elasticity imaging;

If occlusion is deemed insufficient, the applicator may be turned on to reheat the target tissue. High-temperature thermal ablation with coagulation of major structural proteins (large thermal doses), or just thermal necrosis alone (low temperatures or thermal exposures) can be used.

At step 166, the power is then turned off, and the device is removed after target destruction has been completed.

Design criteria for the applicators of the present invention, such as introducer sheaths, catheter OD limits, stiffness constraints, device length, and additional supporting instrumentation, are based on the unique aspects of laparoscopic and hysteroscopic surgeries.

The applicator 50 is configured to treat tissue based on target tissue parameters (e.g. fibroid), and features of the ultrasound transducer (size, frequency, and efficiency), beam distribution, power levels, catheter material, convective cooling, may be varied to account for tissue thermal properties, and dynamic changes in tissue perfusion and ultrasound absorption during thermal exposure.

The acoustic attenuation of fibroids is different than typical soft tissue, and can range from low for necrotic cores to quite high due to the high collagen composition and possibly calcification; the attenuation has been reported to range from 0.9-2.2 dB/cm/MHz, and increase to 1.7-3.3 dB/cm/MHz after HIFU ablation.

Applied power sequences and cooling schemes may also be varied to best control thermal energy penetration to either maximize the thermal lesion 30 size, or to constrain treatment to within a specific radial distance for safety reasons. This includes applied power sequence (ramp, step, pulsed), applied power requirements, and treatment duration.

Experiment #1

Ultrasound interstitial applicators were evaluated for interstitial hyperthermia for combination with radiation or drug therapy, as well as localized thermal ablation. The interstitial ultrasound applicators utilized arrays of small tubular ultrasound radiators, designed to be inserted within plastic implant catheters typically used for interstitial HDR brachytherapy. Water-flow was used during power application to couple the ultrasound and improve thermal penetration. Multi-transducer devices were evaluated with transducer diameters between 1.2 mm-3.5 mm and outer catheter diameters between 2.1 mm (14 gauge) and 4.0 mm (12 Fr), respectively, with 1.5 mm OD transducers and 13 g (2.4 mm OD) catheters the most common configuration. The applicators were fabricated with multiple tubular segments, with separate power control, so that the power deposition or heating pattern could be adjusted in real time along the applicator axis.

The ultrasound energy emanating from each transducer section was highly collimated within the borders of each segment so that the axial length of the therapeutic temperature zone remained well defined by the number of active elements over a large range of treatment duration and applied power levels. FIG. 9 illustrates angular and axial control of power deposition ($P^2$) and heating from in vivo measurements of temperature and zones of thermal coagulation. Thus the applicators of the present invention are ideally suited to tailor temperature distribution in response to anatomy, dynamic changes in perfusion, etc.

Furthermore, the angular or rotational heating pattern, as modified by sectoring the transducer surface, was tested. For example, active zones can be selected (i.e., 90°, 180°, or 360°) to produce angularly selective heating patterns. FIG. 10 illustrates the angular distribution of a 200° applicator. Thus, the orientation of the directional applicators of the present invention can be used to protect critical normal tissue or dynamically rotated and power adjusted to more carefully tailor the regions of heating.

FIG. 11 illustrates the radial depth of the lesion across the axial position of the applicator with respect to the three elements. The multi-element ultrasound applicators were demonstrated to produce contiguous zones of therapeutic temperatures or coagulation between applicators with separation distances of 2-3 cm, while maintaining protection in non-targeted areas. For the interstitial ultrasound devices with tubular sources, the radial penetration of energy falls off as $1/r$ with exponential attenuation and compares favorably to the $1/r^2$ losses of RF needles and $1/r^n$ (n=1-3) losses of microwave antenna. The spatial control along the length of these ultrasound applicators is superior to all other interstitial devices, with axial control defined by active elements over a large range of applied power and durations. Operating at high power levels, single applicators can generate substantial size thermal lesions ex vivo and in vivo up to 21-25 mm radial distance, within 5-10 min treatment times, while maintaining axial and angular control of lesion shape. These ultrasound applicators provide the highest level of controllability, and provide more uniform and penetrating heating than all other interstitial heating techniques.

Because of the higher power levels of the applicator 50, the efficiency and maximum sustainable acoustic output power are important parameters to characterize. The total acoustic power output and conversion efficiency may be measured for varying applicators/transducers using force-balance techniques modified for a cylindrical radiation source. The acoustic efficiency as a function of frequency may then be determined for each applicator 50 using static force-balance measurements. High power output characteristics may then be measured at the frequency of maximum efficiency.

The quality and pattern of the ultrasound energy output may be assessed with acoustic beam distributions. Rotational beam plots (output at 360° around the applicator) may also be measured by 3-D scanning of a calibrated hydrophone system (to measure the acoustic pressure-squared). This distribution of energy output is proportional to the power deposition within tissue, and is therefore a significant characterization to determine thermal therapy potential. Axial, radial, and circumferential fields may be evaluated using iso-intensity contours. These results may also be correlated to shapes of thermal coagulation produced during heating trials ex vivo uterine tissue.

Biothermal acoustic models were developed by our group to study ultrasound applicators for hyperthermia and thermal therapy. The transient finite-difference model is based upon the Pennes Bioheat equation in cylindrical and Cartesian coordinate system. In order to improve accuracy, the model incorporates dynamic tissue changes in response to accumulation of thermal dose. Specifically, when a $t_{43}$=300 min the blood perfusion reduces to zero and at $t_{43}$=600 min the acoustic attenuation increases 1.5-2 times. This dynamic approach has been used to model transurethral 67 and interstitial ultrasound applicators and shown to be in excellent agreement with experiment. The thermal dose distribution using the high-temperature therapy $t_{43}$=240 min is used to define the boundary of thermal necrosis.

The multi-layered model accepts variable convective heat transfer coefficients, heat capacity, thermal conductivity, density, perfusion, and acoustic attenuation within applicator structures and surrounding tissue. The power deposition is determined by either numerical solution of the Rayleigh-Sommerfield diffraction integral using the rectangular radiator method, or by empirical determination of geometric distributions from beam plots.

Simulation of sweeping or rotation of the applicator during the treatment was also performed. The 2D and 3D models have been applied to simulate the anticipated heating patterns. FIG. 12 illustrates maximum temperature contours and lesion shapes for r-z simulations of an interstitial ultrasound applicator heating in vivo thigh muscle for 3 min with (a) one, (b) two, (c) three active transducers. The solid black contour lines represent simulated lesion shapes, and the dashed contour lines represent experimental in vivo measurements of lesions generated after 3 min of heating with 30 W/cm2 applied electrical power per element in pig thigh muscle. FIG. 13 illustrates 3D calculations for a two element interstitial applicator.

The ultrasound applicators of the present invention are amenable to accurate MR image-based treatment planning and thermal monitoring similar to MR-guided focused ultrasound procedures. As shown in FIG. 14, MR thermal imaging can be used to map the temperature elevations and thermal dose (outer contour line) during the application of power/treatment, as demonstrated for high-temperature application in vivo (3 slices, 6 mm apart). FIG. 14 demonstrates thermal ablative temperatures in perfused tissue from cooled 3.5 mm OD transducer array.

To test the ultrasound applicator devices, heating trials were conducted in ex vivo uterine fibroid tissue, obtained directly after surgical removal (hysterectomy or myomectomy). Because fibroids do not naturally develop in the uterine tissue of other mammals, there is no satisfactory animal model to test the applicator performance in a more realistic in vivo environment. Although there is no blood flow in the ex vivo and in vitro tissue samples, imaging studies of uterine fibroids have shown that perfusion in the fibroid tissue is typically low, especially in the center of the tumor where the vasculature has been replaced by a necrotic core. Such heating trials provide a controlled experimental environment where detailed and repeatable tests can be conducted for direct comparison of applicator performance (which is considerably more difficult to achieve in vivo). Thus, the use of ex vivo uterine tissue samples provides the best approximation to the clinical case.

The heating trials were performed with a 2.4 mm OD ultrasound applicator inserted into a pathologic fibroid tissue sample, which was placed in a temperature-controlled water-bath (37° C.). Arrays of miniature thermocouple probes were placed in the tissue, using a template to ensure proper alignment. The probes were multiple junction constantan-manganin sensors, encased in thin-walled polyimide tubing, and inserted within 22-g thin walled needles for minimal thermal conduction and ultrasound artifact. The thermocouples were used to measure radial and axial temperature distributions (and resulting thermal dose) in the tissue, and were recorded using a 32-channel thermometry system with fast data acquisition interfaced to a computer. Placement verification was performed using a portable fluoroscopic unit. Multiple heating trials will be performed with varied applicator parameters of applied power levels, heating times, coolant flows, and active transducer elements for each applicator under test. Following sonication, the tissue was sliced along the transverse and longitudinal axes to measure the boundary and volume of visible thermal coagulation.

The measured radial temperature distributions after 10 minutes of heating using a three element hyperthermia applicator are shown in FIG. 15. As shown in FIG. 15, large volumes of tissue (2.5-3.0 cm radius×3.0 cm length, or ~85 cm$^3$) were thermally destroyed (e.g. temperature >50° C., lethal thermal dose >240 min) using this approach.

Experiment #2

A family of interstitial ultrasound applicators was fabricated using 2-4 cylindrical piezo-ceramic crystal transducers (PZT-4) with outer diameters (OD) of 1.5 or 2.5 mm and lengths of 10-15 mm. The configurations tested were 1.5 mm OD×10 mm long transducers in linear arrays of two, three and four adjacent transducers, an array of three 2.5 mm OD×15 mm long adjacent transducers, and an array of one 2.5 mm OD×15 mm long transducer adjacent to two 2.5 mm OD×10 mm transducers.

The operating frequencies of the transducers ranged from 6.5 to 8 MHz. For some of the applicators, the transducers were sectored to produce a 180° actively acoustic sector for directional power deposition. The transducers were mounted on support structures, and a bio-inert plastic layer was applied for electrical and biological insulation. The 1.5 mm OD applicators were inserted into 13 gage brachytherapy catheters (2.4 mm OD), and the 2.5 mm OD applicators into custom PET catheters (3.7 mm OD). Degassed water was circulated through the applicators to cool the transducers during operation, to couple the ultrasound energy to the tissue, and to potentially control temperature at the tissue-catheter interface allowing for greater radial penetration of thermal energy.

Measurements of electrical impedance (Z) and acoustic efficiency (η) were obtained for each transducer. Z was measured as a function of frequency (5≤f≤10 MHz) using a network analyzer (Hewlett Packard Model #3577A). η was measured as a function of frequency using the force balance technique for cylindrical radiators, and is determined as the ratio of acoustic output power to the applied electrical power. Measurements for the applicators were made with no catheters in place then repeated with the applicators inserted in catheters with a water flow rate of 40 ml/min$^{-1}$. These were used to determine the optimal driving frequencies, and to determine how much acoustic energy is being delivered to the tissue.

The acoustic efficiency data for each transducer type is summarized in Table 1. As expected, there was a 30-40% decrease in η when the applicators were placed in the catheters due to loss of acoustic energy in the catheter wall.

FIG. 16 illustrates the test setup for human uterine fibroids obtained immediately after removal during routine surgical open myomectomies. The fibroids 202 were instrumented with an interstitial ultrasound applicator 210 and six 20 gage thin-walled spinal needles 212 placed at radial distances of 0.5, 1.0, 1.5, 2.0, 2.5, and 3.0 cm from the applicator 210, and scattered in angle for thermometry. A 6 cm×8 cm×1 cm plexiglass template 214 was used to ensure alignment of the applicator 210 and spinal needles 212. The instrumented fibroid 202 was then placed in a 37° C. circulating waterbath 204, and allowed to reach equilibrium. Custom, multi-junction contantan-manganin thermocouple probes consisting of linear arrays of either four 50 µm junctions spaced at 2.5 mm, or seven 50 µm junctions spaced at 5 mm, were inserted into the spinal needles. A 4 channel amplifier with built-in function generator and power monitoring (Advanced Surgical Systems, Inc.) was used to drive the transducers.

Several heating trials were performed to investigate the effects of applicator 210 size (2.4 mm OD vs. 3.7 mm OD), directional heating capability (180° vs. 360° heating patterns), and number and size of active elements 64 (2-4 transducers) on thermal lesion formation (see Table 2). Temperatures were recorded every 3 s at each sensor location (up to 27 data points) using a computer controlled data acquisition system with in-line RF filtering.

FIGS. 17-19 illustrate the results of the heating trial in a human uterine fibroid using a 4-element applicator with 360 degree heating pattern inserted in a 13 g catheter with 60 ml/min flow rate (f=8.2-8.5 MHz, 15 W to three elements for 8 minutes). FIG. 17 shows the measured transient temperature curves (each curve represents the average of 4 sensors at each radial depth of 0.5, 1.0, 1.5, 2.0, 2.5, and 3.0 cm). FIG. 18 is a graph of the radial temperature distribution after heating for 2, 4, 6 and 8 minutes, and average accumulated thermal dose at each radial depth after heating for 8 minutes. FIG. 19 is the temperature distribution measured at 1 cm radial distance along the length of the applicator with 3 active elements at 2 minute time intervals.

The accumulated iso-effect thermal dose was calculated from the temperature-time history at each point according to:

$$t_{43} = \sum_{t=0}^{t=final} R^{(T-43)} \Delta t$$

where $t_{43}$ is the equivalent time at 43° C., T is the average temperature during time Δt, and R is a constant based on the activation energy and absolute temperature from the Arrhenius relationship (R=2 for T≥43° C., R=4 for T<43° C.).

After heating, the tissue was sliced into sections approximately 5-10 mm thick. Since the thermal lesions were not clearly visible, the tissue sections were placed into a 2% solution of 2,3,5-triphenyltetrazolium chloride (TTC) for approximately 20 minutes. TTC is a tissue viability stain that allows for visualization of acute, lethal tissue damage at a macroscopic level. Measurements of visible thermal lesions were then obtained, and the tissue sections then placed in a 10% buffered Formalin solution for fixation, and later sectioning. Standard hematoxylin and eosin (H&E) stained sections were obtained for histological evaluation.

FIG. 20 illustrates a sagittal slice through thermal lesion 30, visualized after 20 minutes in a 2% TTC solution (measured dimensions=3.5 cm diameter×3.9 cm long).

FIGS. 21 and 22 illustrate transverse slices through thermal lesions (as isualized using TTC stain) generated in human uterine fibroids using a 3-element applicator with a 180 degree directional heating pattern, inserted in a 3.7 mm OD catheter with 60 ml/min flow rate (f=6.6-7.6 MHz). FIG. 21 illustrates a directional lesion produced by 15 W to two elements for 7 minutes (fibroid was at thermal equilibrium in a 28° C. waterbath; lesion radius=1.2 cm). Maximum temperatures measured at radial distances of 0.5, 1.0, and 1.5 cm from the applicator are shown with corresponding accumulated thermal dose.

FIG. 22 is a directional lesion produced by 15 W to three elements for 15 minutes (lesion radius=1.7 cm). Maximum temperatures measured at radial distances of 0.5, 1.0, 1.5, 2.0, and 2.5 cm from the applicator are shown with corresponding accumulated thermal dose. Position of the applicator and direction of energy delivery are shown by the white circle with arrow for both FIGS. 21 and 22.

FIGS. 23 and 24 illustrate H&E stained sections of human uterine fibroid tissue (at 400× magnification). FIG. 23 illustrates untreated tissue showing lighter, heterogeneous and slightly granular chromatin, and visible nuclear features. FIG. 24 shows treated tissue indicating hyperchromatic nuclei with no visible features and homogenously dark chromatin. Cytoplasm also appears slightly darker than the untreated tissue.

FIGS. 25-28 illustrate additional tests performed with varying applicators and distribution patterns. FIG. 25 illustrates a three–10 mm transducer applicator and resulting tissue lesion. The size of the lesion in FIG. 25 is directly correlated to the applicator transducer geometry, particularly when compared to the lesion achieved by the four–10 mm transducer applicator shown in FIG. 26. FIG. 27 illustrates a lesion created by a two–10 mm transducer applicator with 180° directional distribution. FIG. 28 further illustrates a 180° directional distribution applicator applied at an insertion point.

Results from this study demonstrated that thermal lesions greater than 1.5-1.7 cm radial depth (3-3.5 cm diameter) and up to 5 cm in length (as evidenced by staining with TTC) could be produced in human fibroid tissue in less than 10 min with 15 W of applied electrical power. Further, therapeutic temperatures greater than 50° C., and potentially lethal thermal doses extended beyond 2.0 cm radially from the applicator (>4 cm diameter). Histological examination of heated tissue revealed hyperchromatic nuclei with homogeneously dark chromatin, and no visible nuclear features, as compared to untreated tissue.

In conclusion, high-intensity interstitial ultrasound thermal treatment of uterine fibroids can potentially be used to access treatment of more fibroids and patients than possible with existing technologies, and provide a safer easier approach with lower morbidity, shorter treatment duration, and lower procedure costs.

Interstitial ultrasound provides exceptional control over the heating length and radial depth, and ability to have selective heating patterns provides an innovative interstitial thermal ablation technology that can be applied to treat fibroids more consistently, more thoroughly, and faster following procedures that can be routinely applied by gynecological surgeons. This superior spatial control can be used to safely target a larger number of fibroids than can be treated with existing ablative technology. Interstitial ultrasound technology provides the ability to treat a targeted fibroid region while simultaneously protecting other non-targeted healthy tissue.

It is believed that thermal myolysis may preserve the integrity of the uterine wall with uncomplicated full-term pregnancies and uneventful vaginal deliveries post procedure are reported. This indicates that minimally-invasive thermal ablation of uterine fibroids may become a treatment of choice for women still considering having children, significantly increasing the number of patients that could benefit from precise and selective high-intensity interstitial ultrasound treatment.

Only certain fibroids can be removed by laparoscopy. If the fibroids are large, numerous, or deeply embedded in the uterus, then an abdominal myomectomy or hysterectomy may be necessary. With laparoscopic interstitial thermal ablation, these fibroids that are too large for surgical removal can be treated in situ in a minimally-invasive fashion. A single insertion of an interstitial ultrasound applicator can treat larger fibroids than possible with multiple insertions of existing technology.

In addition, it is proposed that thermal ablation and resultant thermal fixation of tissue produces a faster less painful recovery compared to the painful ischemic necrosis of fibroids and uterine tissue encountered in patients post-UAE procedures.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Acoustic efficiency (η) data for the three transducer geometries used in this study. Measurements were made without catheters, then repeated with catheters (flow rate = 40 ml/min).

| Transducer Description | f (MHz) | η (no catheter) | η (in catheter) | Catheter |
| --- | --- | --- | --- | --- |
| 1.5 mm OD × 10 mm long | 7.2 | 52% | 32% | 2.4 mm OD |
| 2.5 mm OD × 10 mm long | 6.6 | 59% | 35% | 3.7 mm OD |
| 2.5 mm OD × 15 mm long | 7.6 | 62% | 36% | 3.7 mm OD |

TABLE 2

Thermal lesion dimensions measured using different applicator configurations

| # Elements | Applicator/Catheter | Power (W) | Time (min) | Lesion Dimensions (cm) |
| --- | --- | --- | --- | --- |
| 4 | 1.5 mm OD/2.4 mm OD | 15 per chan. | 8 | 3.5 dia. × 5.0 long[a] |
| 3 | 1.5 mm OD/2.4 mm OD | 15 per chan. | 8 | 3.5 dia. × 3.9 long[a] |
| 2 | 1.5 mm OD/2.4 mm OD | 12 per chan. | 8 | 1.5 rad. × 2.5 long[b] |
| 3 | 2.5 mm OD/3.7 mm OD | 15 per chan. | 15 | 1.7 rad.[b] |
| 2 | 2.5 mm OD/3.7 mm OD | 15 per chan. | 7 | 1.2 rad.[b,c] |

Notes:
[a]360 degree heating pattern;
[b]180 degree directional heating pattern;
[c]Tissue was at thermal equilibrium in a 28° C. waterbath rather than a 37° C. waterbath resulting in smaller lesion size

What is claimed is:

1. An apparatus for treating uterine fibroids, comprising:
   (a) a catheter having a distal end and a proximal end; and
   (b) an ultrasound applicator disposed at the distal end of said catheter, the ultrasound applicator comprising:

a plurality of transducers disposed longitudinally along a central axis of the catheter;
the one or more transducers being coupled to a power source external to said catheter;
(c) wherein the ultrasound applicator is configured to be positioned at a treatment location interstitially within a fibroid tissue mass and deliver high-intensity ultrasound energy outward into said fibroid tissue mass sufficient to therapeutically heat said fibroid tissue mass;
(d) wherein each of the one or more transducers are sectored into a plurality of segments such that at least one wired radial segment emits a portion of a 360° radial pattern to provide directional energy distribution of the ultrasound energy in a first direction associated with the fibroid while a second radial segment limits or emits no ultrasound energy in a second direction; and
(e) wherein each segment is individually wired to a power source such that each segment may be operated at a different power level and frequency than the other segments.

2. An apparatus as recited in claim 1, wherein the delivered energy is sufficient to ablate the fibroid tissue.

3. An apparatus as recited in claim 1, wherein the delivered energy is sufficient to necrose the fibroid tissue.

4. An apparatus as recited in claim 1, wherein the applicator is configured such that sufficient energy is applied to treat the fibroid tissue within a period ranging between approximately 3 to 20 minutes.

5. An apparatus as recited in claim 1, wherein the applicator comprises an array of two to five transducers.

6. An apparatus as recited in claim 5, wherein the applicator comprises an array of three to four transducers.

7. An apparatus as recited in claim 1, wherein the transducers are tubular and disposed adjacent each other over a support element in a linear array.

8. An apparatus as recited in claim 1, wherein the one or more transducers comprises a single tubular transducer that is scored to form the one or more wired radial segments.

9. An apparatus as recited in claim 7, wherein the ultrasound transducers are disposed within the catheter.

10. An apparatus as recited in claim 7, wherein the ultrasound transducers are disposed adjacent to the distal end of the catheter.

11. An apparatus as recited in claim 10, wherein the catheter is configured to provide fluid cooling to the ultrasound elements.

12. An apparatus as recited in claim 11:
wherein the applicator further comprises a balloon emanating at the distal end of the catheter; and
wherein the balloon is configured to surround the one or more transducers to circulate the cooling fluid around the one or more transducers.

13. An apparatus as recited in claim 11, wherein the catheter comprises a multi-lumen catheter with a first lumen configured to deliver fluid to the applicator, and a second lumen configured to transport fluid out of the applicator.

14. An apparatus as recited in claim 1, further comprising a retractable sheath configured to surround the applicator during delivery to the treatment site.

15. An apparatus as recited in claim 1, further comprising a temperature probe disposed at the distal end of the catheter, the temperature probe configured to acquire temperature readings at one or more locations of tissue in vicinity to the applicator.

16. An apparatus as recited in claim 7:
wherein the catheter comprises a bendable portion proximal to the applicator such that the applicator may be oriented at an angle with respect to the catheter proximal to the bendable portion; and
wherein the bendable portion comprises a material configured to retain said angle as the applicator is delivered to the treatment site.

17. An apparatus as recited in claim 1, wherein the applicator is configured to be delivered laparoscopically.

18. An apparatus as recited in claim 1, wherein the applicator is configured to be delivered hysteroscopically.

19. An apparatus as recited in claim 1, wherein the one or more transducers have an emission surface configured to direct the ultrasound energy transmission radially outward as a collimated or diverging beam at the fibroid tissue mass.

20. An apparatus as recited in claim 19, wherein the applicator is configured to be swept across a path to deliver ultrasound energy across a volume of the fibroid tissue.

21. A method of treating a uterine fibroid, comprising:
interstitially positioning an ultrasound transducer at a treatment location within a fibroid tissue mass; and
administering power to the transducer to deliver high-intensity ultrasound energy outward into the fibroid tissue mass;
wherein the power is delivered independently to a first radial segment of the transducer to emit a portion of a 360° radial pattern that delivers directional energy at a first direction associated with the fibroid, while limiting or cutting power to a second radial segment of the transducer to shield ultrasound energy delivery in a second direction;
wherein each segment is independently operated with different power level and frequency control than the other segments; and
wherein said ultrasound energy is sufficient to therapeutically heat said fibroid tissue mass.

22. A method as recited in claim 21, wherein said delivered ultrasound energy is sufficient to ablate the fibroid tissue.

23. A method as recited in claim 21, wherein said delivered ultrasound energy is sufficient to necrose the fibroid tissue.

24. A method as recited in claim 21, wherein prior to delivery of the ultrasound energy, the power, treatment time, and frequency of the ultrasound energy is determined based on the fibroid tissue anatomy.

25. A method as recited in claim 21, wherein the ultrasound energy is delivered directly to an adjacent portion of the fibroid tissue, said portion comprising feeding vasculature.

26. A method as recited in claim 21, further comprising:
deploying a thermal sensor to obtain temperature feedback of tissue at or near the applicator.

27. A method as recited in claim 21, further comprising:
determining the extent of therapy by applying one or more of the following diagnostic techniques: fluoroscopy, Doppler ultrasound, MRI, or CT imaging.

28. A method as recited in claim 25, wherein the ultrasound energy is delivered as a collimated or diverging beam to the fibroid tissue.

29. A method as recited in claim 21, wherein positioning an ultrasound applicator comprises directing the ultrasound applicator to the treatment location at the distal end of a catheter.

30. A method as recited in claim 29, wherein the applicator is guided to the treatment location with one or more of the following imaging techniques: fluoroscopy, Doppler ultrasound, MRI, or CT imaging.

31. A method as recited in claim 21:
wherein the ultrasound transducer comprises a longitudinal array of independent transducers;

wherein the transducers are individually operated to independently or concurrently deliver ultrasound energy; and wherein the energy is delivered at different intensities to the independent transducers in the longitudinal array according to the shape of the fibroid.

32. A method as recited in claim 29:
wherein the applicator is delivered to a location substantially adjacent the fibroid tissue; and
wherein the applicator emits ultrasound energy in a radial pattern less than 360°.

33. A method as recited in claim 32, wherein the applicator emits ultrasound energy in a radial pattern of approximately 180° or less.

34. A method as recited in claim 29, wherein the applicator emits ultrasound energy in a focused pattern at a location within the fibroid tissue.

35. A method as recited in claim 29, further comprising:
delivering a cooling fluid to the applicator through the catheter during delivery of ultrasound energy.

36. A method as recited in claim 35:
wherein delivering a cooling fluid comprises delivering the cooling fluid into a balloon emanating at the distal end of the catheter; and
wherein the balloon is configured to surround the one or more transducers to circulate the cooling fluid around the one or more transducers.

37. A method as recited in claim 21, wherein positioning an ultrasound transducer at a treatment location comprises laparoscopically delivering the transducer to the treatment location.

38. A method as recited in claim 21, wherein positioning an ultrasound transducer at a treatment location comprises hysteroscopically delivering the transducer to the treatment location.

39. An apparatus for treating uterine fibroids, comprising:
(a) a catheter having a distal end and a proximal end;
(b) an ultrasound applicator disposed at the distal end of said catheter, the ultrasound applicator comprising:
at least one tubular transducer disposed longitudinally over a support element;
said support element being substantially coincidental with a central axis of the catheter; and
(c) a power source external to said catheter;
(d) said power source being coupled to the at least one tubular transducer;
(e) wherein the ultrasound applicator is configured to be interstitially positioned at a treatment location within a fibroid tissue mass to deliver high-intensity ultrasound energy directly outward into said fibroid tissue mass sufficient to heat and destroy the fibroid tissue mass;
(f) wherein the transducer is sectored into a plurality of segments such that at least one wired radial segment emits a portion of a 360° radial pattern to provide directional energy distribution of the ultrasound energy in a first direction associated with the fibroid while a second radial segment limits or emits no ultrasound energy in a second direction;
(e) wherein each segment is individually wired to the power source such that each segment may be individually operated at a different power level and frequency than the other segments.

40. An apparatus as recited in claim 39, wherein the applicator comprises an array of two to five transducers disposed adjacent each other in a longitudinal array.

41. An apparatus as recited in claim 40, wherein the applicator comprises an array of three to four transducers.

42. An apparatus as recited in claim 39, wherein the transducer is configured to emit in a radial pattern less than 180°.

43. An apparatus as recited in claim 39, wherein the transducer is sectored into a plurality of individually wired radial segments that each emit an independently operable portion of a 360° radial pattern.

44. An apparatus as recited in claim 39, wherein the ultrasound transducers are disposed within the catheter.

45. An apparatus as recited in claim 39, wherein the ultrasound transducers are disposed adjacent to the distal end of the catheter.

46. An apparatus as recited in claim 44, wherein the catheter is configured to provide fluid cooling to the ultrasound elements.

47. An apparatus as recited in claim 46:
wherein the applicator further comprises a balloon emanating at the distal end of the catheter; and
wherein the balloon is configured to surround the one or more transducers to circulate the cooling fluid around the one or more transducers.

48. An apparatus as recited in claim 39, further comprising:
a temperature probe disposed at the distal end of the catheter;
wherein the temperature probe is configured to acquire temperature readings at one or more locations of tissue in vicinity to the applicator.

\* \* \* \* \*